United States Patent
Tsai et al.

(10) Patent No.: US 12,428,675 B2
(45) Date of Patent: *Sep. 30, 2025

(54) REAGENTS AND METHODS FOR BLOCKING NON-SPECIFIC INTERACTIONS WITH NUCLEIC ACIDS

(71) Applicant: Enable Biosciences Inc., South San Francisco, CA (US)

(72) Inventors: Cheng-Ting Tsai, South San Francisco, CA (US); Peter Robinson, South San Francisco, CA (US)

(73) Assignee: Enable Biosciences Inc., South San Francisco, CA (US)

( * ) Notice: Subject to any disclaimer, the term of this patent is extended or adjusted under 35 U.S.C. 154(b) by 120 days.

This patent is subject to a terminal disclaimer.

(21) Appl. No.: 17/349,090

(22) Filed: Jun. 16, 2021

(65) Prior Publication Data
US 2021/0310049 A1    Oct. 7, 2021

Related U.S. Application Data

(63) Continuation of application No. 16/905,405, filed on Jun. 18, 2020, now Pat. No. 11,053,538, which is a continuation of application No. PCT/US2019/014570, filed on Jan. 22, 2019.

(60) Provisional application No. 62/622,958, filed on Jan. 28, 2018.

(51) Int. Cl.
*C12Q 1/686* (2018.01)
(52) U.S. Cl.
CPC ....... *C12Q 1/686* (2013.01); *C12Q 2537/163* (2013.01)
(58) Field of Classification Search
None
See application file for complete search history.

(56) References Cited

U.S. PATENT DOCUMENTS

| | | | |
|---|---|---|---|
| 9,677,131 B2 | 6/2017 | Fredriksson et al. | |
| 11,053,538 B2* | 7/2021 | Tsai | C12Q 1/686 |
| 2002/0142339 A1* | 10/2002 | Bardhan | B01J 20/28083 |
| | | | 205/777.5 |
| 2004/0023248 A1 | 2/2004 | O'Malley | |
| 2013/0171652 A1 | 7/2013 | Fredriksson et al. | |
| 2016/0131604 A1 | 5/2016 | Easley et al. | |
| 2016/0265031 A1* | 9/2016 | Liu | C12Q 1/6806 |

FOREIGN PATENT DOCUMENTS

| | | |
|---|---|---|
| WO | WO 2010/115046 A2 | 10/2010 |
| WO | WO 2010/115046 A3 | 10/2010 |
| WO | WO 2012/007511 A1 | 1/2012 |

OTHER PUBLICATIONS

Caminade, Uses of Dendrimers for DNA Microarrays, Sensors, 6(8): 901-914, 2006. (Year: 2006).*
Yabbarov, Polyamidoamine Dendrimers with Different Surface Charge as Carriers in Anticancer Drug Delivery, Russian Journal of Bioorganic Chemistry, 43(2): 155-162, 2017. (Year: 2017).*
International Search Report for PCT/US2019/014570 dated Apr. 11, 2019.
Day, "Thiolated Dendrimers as Multi-Point Binding Headgroups for DNA Mobilization on Gold," Langmuir, 27(20): 12434-12442, 2011.
International Search Report mailed Apr. 11, 2019 in International Application No. PCT/US2019/014570.
Office Action dated Oct. 1, 2021 in European Application No. 19707514.6.

* cited by examiner

*Primary Examiner* — Gary Benzion
*Assistant Examiner* — Carolyn L Greene
(74) *Attorney, Agent, or Firm* — Knobbe Martens Olson & Bear LLP

(57) ABSTRACT

Methods and reagents for blocking non-specific interactions with nucleic acids are disclosed. In particular, the invention relates to multi-valent blockers comprising multiple negatively charged polymers or materials attached to a common scaffold and their use in blocking non-specific interactions with nucleic acids.

11 Claims, 11 Drawing Sheets

Specification includes a Sequence Listing.

Multivalent negative charge blocker

Multivalent nucleotide  Multivalent negative charge polymer (e.g. polyacrylic acid)

REAGENTS AND METHODS FOR BLOCKING NON-SPECIFIC INTERACTIONS WITH NUCLEIC ACIDS

CROSS REFERENCE TO RELATED APPLICATIONS

This application is a continuation of U.S. patent application Ser. No. 16/905,405 filed Jun. 18, 2020, which issued as U.S. Pat. No. 11,053,538 on Jul. 6, 2021, which is a continuation of PCT/US2019/014570, filed Jan. 22, 2019, entitled "REAGENTS AND METHODS FOR BLOCKING NON-SPECIFIC INTERACTIONS WITH NUCLEIC ACIDS," which designated the United States and was published in the English language, and which claims the benefit of priority to U.S. Provisional Application Ser. No. 62/622,958, filed Jan. 28, 2018, entitled "REAGENTS AND METHODS FOR BLOCKING NON-SPECIFIC INTERACTIONS WITH NUCLEIC ACIDS," all of which are hereby expressly incorporated by reference in their entirety and for all purposes.

TECHNICAL FIELD

The present invention pertains generally to reagents and methods for blocking non-specific interactions with nucleic acids. In particular, the invention relates to multivalent blockers comprising multiple negatively charged polymers or materials attached to a common scaffold and their use in blocking non-specific interactions with nucleic acids.

REFERENCE TO SEQUENCE LISTING

The material in the accompanying sequence listing is hereby expressly incorporated by reference in its entirety into this application. The accompanying sequence listing text file, named SeqList-ENBIO-001C2.txt, was created on Jun. 16, 2021, and is 569 bytes in size. The content of the sequence listing is hereby expressly incorporated by reference in its entirety.

BACKGROUND

Since the discovery of the structure of DNA by Watson and Crick, medical and biological fields have advanced significantly. Groundbreaking innovations have leveraged the unique biological roles and chemical properties of nucleic acids. Chemically tailored nucleic acids (e.g., DNA, siRNA, nucleic acid derivatives) permit the efficient transfer of new genetic information into the target cells as a powerful therapeutic strategy [1]. Gene editing methods such as Crispr-Cas9 use specialized RNA-guided protein machinery to delete, insert, and directly modify DNA for research and therapeutic applications. In addition, bespoke nucleic acid sequences like aptamers form unique conformational structures to bind target proteins with high specificity and affinity as a promising alternative to traditional antibody therapeutics [2]. Thus, it is evident that nucleic acid-based technologies are foundational to many emerging therapies, and prevention of non-specific binding to these nucleic acid materials is critical for enhancement of drug efficacy and reduction of off-target effects.

On the other hand, nucleic acid technologies also serve as powerful analytical tools for biomedical research and diagnostics. Indeed, nucleic acids are widely-used as barcodes in multiplex analysis of biological specimens. For instance, Nanostring has successfully used fluorescent DNA barcoding to develop molecular diagnostic assays such as their nCounter panel [3]. Other companies such as Somalogic use nucleic acid aptamers as antibody surrogates to create impressively large (>1300 members) protein arrays. These innovations successfully use nucleic acid barcoding to greatly expand the multiplexibility of analytical assays [4]. Prevention of non-specific binding to these nucleic acid barcodes is thus essential for maintaining high specificity in such multiplex assays.

Apart from their use as barcodes, nucleic acids have been used to substantially enhance the sensitivity of analytical assays. Immuno-PCR leverages the exponential amplification power of polymerase to augment signal amplification to achieve close to single-molecule-level sensitivity. Moreover, newer generations of PCR-based immunoassays have been devised, such as antibody detection by agglutination-PCR (ADAP), to improve sensitivity while simplifying assay workflow [5]. This innovation opens the possibility of detecting disease-relevant biomarkers at an earlier stage, increasing treatment options and effectiveness to improve patient outcomes. Notably, even very weak non-specific binding of nucleic acid materials is likely to cause detectable background signals in these highly sensitive assays, thereby compromising assay specificity.

Additionally, many nucleic acid-based assays use the ability of nucleic acids to rapidly and faithfully bind to its reverse-complement as a mechanism of detection. For instance, complementary nucleic acid strands could be installed on solid surface, capturing its reverse complement molecule present in a biological specimen through a hybridization reaction. Then, a secondary reporter can be added to generate signals. These secondary reporters could generate signals through diverse means, such as fluorescent signals (by tagging fluorescent tags), electronic signals (by tagging molecules capable of generating electrons) or magnetic signals (by tagging magnetic particles). The assay workflows may or may not require washing steps to remove unbound secondary reporter. Companies such as Affimetrix (fluorescent arrays), T2 Biosystems (magnetic signals) [6], Genmark (electric signals) [7], DNAc (electric signals) employ such mechanisms in their products. Genomic elements can also be directly labelled in biospecimen to simultaneous quantify gene expression and localization. A widely-used version of this approach is fluorescence in situ hybridization (FISH), which is commonly employed for tissue slices. Finally, recent technology advanced by company such as InCellDx also allows fluorescence in situ hybridization on intact cells, thereby allowing downstream flow cytometry analysis [8]. As a whole, these assays rely on highly-specific interactions between nucleic acids and their reverse-complementary strands to achieve detection of biomolecules in a complex environment. As a result, prevention of nonspecific binding to nucleic acid materials are instrumental to maintain these assays' specificity.

Finally, advancement of next-generation sequencing (NGS) methods has revolutionized biomedical research. A critical component of NGS is library preparation. Library preparation refers to a process from which initial nucleic acid materials in a biospecimen is converted to NGS compatible format. Today's technologies permit library preparation from ultra-low sample inputs (e.g. 10 pg RNA input), and even down to the single cell levels in some cases [9]. Prevention of non-specific binding of nucleic acid materials would greatly increase the library preparation yield (e.g. increase the percentage of single cells from which a successful NGS library could be obtained by preventing loss of genomic materials due to non-specific binding to lab consumables). In addition, many NGS methods require binding of nucleic acid library materials onto a solid support (e.g. 454 (Roche), SOLID (Thermo Fisher), GeneReader (Qiagen), Ion Torrent (Thermo Fisher), Illumina, and Complete Genomics BGI). The solid support could be a microarray array, a bead, a glass slide or a structured solid substrate. Again, non-specific anchoring of genomic materials onto these solid supports would create biased and unwanted background signals in the sequencing process, and should be prevented. Furthermore, recent advancement of analytical methods allows use of nucleic acid-barcoded antibodies to achieve simultaneous single-cell analysis of protein and RNA expression [9]. Similarly, nucleic acid-barcoded MHC tetramers have been used to interrogate T cell receptor specificity and corresponding gene expression simultaneously [10]. These methods again largely require a method to reduce non-specific binding of nucleic acid barcoded materials onto cells being analyzed, thereby reducing unwanted background signals.

However, several universal challenges remain for prevention of non-specific nucleic acid binding. Nucleic acids bear a strong negative charge due to phosphate groups that compose the molecule's backbone. This negative charge confers an electrostatic affinity to positively charged molecules in a sequence- and barcode-independent manner. This charge affinity is a major source of unwanted non-specific interactions, leading to (1) nucleic acid therapies or diagnostic probes sequestered in undesired locations, thereby reducing actual dosing in the target cells (2) nucleic acid analytical reagents creating nonspecific and off-target signals, leading to false positives and negatives (3) reduction of yield in single cell or ultra-low sample input next-generation sequencing experiments. These issues greatly reduce the reliability of therapeutics, research or diagnostics tools based on nucleic acid materials. The current state of the art employs excess inert single-stranded or double-stranded nucleic acids as blocking agents to prevent non-specific interactions between precious functional nucleic acids and other molecules [9]. Common sources of these state of the art blocking agents are extracted DNA or RNA from salmon sperm or *E. coli*. However, in many circumstances, these biologically derived blocking agents suffer from varying compositions from batch to batch, and still cannot fully prevent non-specific binding in many cases [9]. In addition, charged detergents such as sodium dodecyl sulfate (SDS) and dextran sulfate are also used to achieve a similar result [9]. Nevertheless, it is widely reported that these detergents could either denature protein components in the system, or could inhibit downstream applications (e.g. PCR), thereby introducing their own interferences. In summary, though these important state of the art methods have facilitated the use of nucleic acid technologies, their abilities to abrogate non-specific binding of nucleic acids materials are limited. It is well-known in the field that the applications of nucleic acids materials mentioned above still suffer from specificity and off-target issues. Thus, there remains a need for better methods of blocking non-specific interactions between nucleic acids and other molecules.

SUMMARY

The present invention is based on the development of reagents and methods for blocking non-specific interactions with nucleic acids.

In one aspect, the invention includes method of blocking non-specific interactions with a nucleic acid of interest in a sample, the method comprising contacting the sample with a multivalent blocker, said multivalent blocker comprising at least two negatively charged polymers linked to a scaffold, wherein the multivalent blocker binds to positively charged compounds or materials in the sample, thereby blocking non-specific interactions with the nucleic acid of interest.

In certain embodiments, 2-10 or more negatively charged polymers may be linked to the scaffold, including any number of negatively charged polymers in this range, such as 1, 2, 3, 4, 5, 6, 7, 8, 9, 10, or more negatively charged polymers. The polymers linked to the scaffold, for example, may comprise one or more negatively charged functional groups such as, but not limited to, carboxylate, sulfate, and phosphate groups. The negatively charged polymers can be linked to the scaffold covalently or noncovalently.

In certain embodiments, the polymers linked to the scaffold are nucleic acids. For example, 2-10 or more nucleic acids may be linked to the scaffold, including any number of nucleic acids in this range, such as 1, 2, 3, 4, 5, 6, 7, 8, 9, 10, or more nucleic acids.

In other embodiments the negatively charged polymer is a poly(acrylic acid) polymer. For example, 2-10 or more negatively charged poly(acrylic acid) polymers may be linked to the scaffold, including any number of negatively charged poly(acrylic acid) polymers in this range, such as 1, 2, 3, 4, 5, 6, 7, 8, 9, 10, or more poly(acrylic acid) polymers.

In certain embodiments the scaffold is a dendrimer (e.g., polyamidoamine (PAMAM) dendrimer), a multi-armed polyethylene glycol (PEG), a nanoparticle (e.g., gold nanoparticles), or streptavidin.

In certain embodiments, the scaffold is spherical (e.g., beads, pellets), nonspherical (e.g., non-spherical nano- and micro-scale particles), linear (e.g., linear polymers or fibers), branched (e.g. 2 or more branches with binding sites for negatively charge polymers), or planar (e.g., thin sheet, membrane, or plate). The scaffold may range in size from about 0.3 nm to about 5 nm in length, including any length in this range such as 0.3 nm, 0.4 nm, 0.5 nm, 0.75 nm, 1 nm, 1.5 nm, 2 nm, 2.5 nm, 3 nm, 3.5 nm, 4 nm, 4.5 nm, or 5 nm.

In certain embodiments, the nucleic acid of interest is a nucleic acid probe comprising a detectable label. In another embodiment, the multivalent blocker further comprises the same detectable label as the nucleic acid probe. The detectable label can be, for example, a fluorescent, bioluminescent, or chemiluminescent label, and may be attached to the scaffold or a negatively charged polymer linked to the scaffold.

In certain embodiments, the method further comprises performing real time quantitative polymerase chain reaction (RT-PCR), microarray analysis, fluorescent in situ hybridization (FISH), a NanoString assay, next generation sequencing, fluorescence resonance energy transfer (FRET), T2 magnetic resonance (T2MR), antibody-detection by agglutination PCR (ADAP), CRISPR-CAS9 genome editing, or transfection while blocking the non-specific interactions with the nucleic acid of interest.

In certain embodiments, the nucleic acid of interest is conjugated to an agent such as, but not limited to, an antibody, an antigen, a peptide, a protein, a lipid, a carbohydrate, a small molecule, a nanoparticle, or a cationic molecule. In certain embodiments, the nucleic acid of interest is DNA or RNA. For example, the nucleic acid of interest may be an RNA selected from the group consisting of messenger RNA (mRNA), transfer RNA (tRNA), ribosomal RNA (rRNA), small interfering RNA (siRNA), microRNA (miRNA), short hairpin RNA (shRNA), small nuclear RNA (snRNA), and long noncoding RNA (lncRNA).

In another example, the nucleic acid of interest is a DNA aptamer or RNA aptamer. In another aspect, the invention includes a composition comprising a multivalent blocker comprising at least two negatively charged polymers or materials linked to a scaffold, as described herein.

In certain embodiments, the composition comprises a multivalent blocker comprising at least one nucleic acid linked to the scaffold, wherein at least one nucleic acid comprises the nucleotide of SEQ ID NO:1 sequence (5'-TCGTGGAACTATCTAGCGGTGTACGTGAGTGGG-CATGTAGCAAGAGGGTC-3' (SEQ ID NO: 1), or a sequence displaying at least about 80-100% sequence identity thereto, including any percent identity within this range, such as 81, 82, 83, 84, 85, 86, 87, 88, 89, 90, 91, 92, 93, 94, 95, 96, 97, 98, 99% sequence identity thereto, wherein the multivalent blocker is capable of blocking nonspecific interactions with a nucleic acid of interest in a sample.

In another embodiment, the composition further comprises one or more nucleic acids of interest.

In another embodiment, the composition further comprises one or more reagents for performing real time quantitative PCR, microarray analysis, fluorescent in situ hybridization (FISH), a NanoString assay, next generation sequencing, fluorescence resonance energy transfer (FRET), T2 magnetic resonance (T2MR), antibody-detection by agglutination PCR (ADAP), or CRISPR-CAS9 genome editing, or transfection.

In another embodiment, the invention includes a kit comprising a multivalent blocker described herein and instructions for using the multivalent blocker for blocking non-specific interactions with a nucleic acid if interest in a sample. In another embodiment, the kit further comprises one or more reagents for performing real time quantitative PCR, microarray analysis, fluorescent in situ hybridization (FISH), a NanoString assay, next generation sequencing, fluorescence resonance energy transfer (FRET), T2 magnetic resonance (T2MR), antibody-detection by agglutination PCR (ADAP), or CRISPR-CAS9 genome editing, or transfection.

Preferred alternatives of the invention include the following.

1. A method of blocking non-specific interactions with a nucleic acid of interest in a sample, the method comprising contacting the sample with a multivalent blocker, said multivalent blocker comprising at least two negatively charged polymers linked to a scaffold, wherein the multivalent blocker binds to positively charged compounds or materials in the sample, thereby blocking non-specific interactions with the nucleic acid of interest.
2. The method of alternative 1, wherein 2-10 negatively charged polymers are linked to the scaffold.
3. The method of alternative 1 or 2, wherein 5 negatively charged polymers are linked to the scaffold.
4. The method of anyone of alternatives 1-3, wherein the negatively charged polymers linked to the scaffold are nucleic acids, poly(acrylic acid) polymers, polysaccharides, or peptides.
5. The method of alternative 4, wherein the nucleic acids linked to the scaffold are RNA or DNA.
6. The method of any one of alternatives 1-5, wherein the negatively charged polymers linked to the scaffold comprise negatively charged functional groups.
7. The method of alternative 6, wherein the negatively charged functional groups are selected from the group consisting of carboxylate, sulfate, and phosphate.
8. The method of anyone of alternatives 1-7, wherein the scaffold comprises a dendrimer, a protein, a multiarmed polyethylene glycol (PEG), or a nanoparticle.
9. The method of alternative 8, wherein the dendrimer is a polyamidoamine (PAMAM) dendrimer.
10. The method of alternative 8, wherein the protein is streptavidin or avidin.
11. The method of alternative 8, wherein the nanoparticle is a gold nanoparticle.
12. The method of anyone of alternatives 1-11, wherein the scaffold is spherical, nonspherical, linear, branched, or planar.
13. The method of anyone of alternatives 1-12, wherein the scaffold has a size ranging from about 0.3 nm to about 5 nm in length.
14. The method of anyone of alternatives 1-13, wherein the negatively charged polymers are linked to the scaffold covalently or noncovalently.
15. The method of anyone of alternatives 1-14, wherein the nucleic acid of interest is a nucleic acid probe comprising a detectable label.
16. The method of alternative 15, wherein the multivalent blocker further comprises the same detectable label as the nucleic acid probe.
17. The method of alternative 15 or 16, wherein the detectable label is a fluorescent, bioluminescent, or chemiluminescent label.
18. The method of anyone of alternatives 1-17, further comprising performing real time quantitative polymerase chain reaction (RT-PCR), microarray analysis, fluorescent in situ hybridization (FISH), a NanoString assay, next generation sequencing, fluorescence resonance energy transfer (FRET), T2 magnetic resonance (T2MR), antibody-detection by agglutination PCR (ADAP), CRISPR-CAS9 genome editing, or transfection while blocking the non-specific interactions with the nucleic acid of interest with the multivalent blocker.
19. The method of anyone of alternatives 1-18, wherein the nucleic acid of interest is conjugated to an agent.
20. The method of alternative 19, wherein the agent is an antibody, an antigen, a peptide, a protein, a lipid, a carbohydrate, a small molecule, a nanoparticle, or a cationic molecule.
21. The method of anyone of alternatives 1-20, wherein the nucleic acid of interest is DNA or RNA.
22. The method of alternative 21, wherein the RNA is selected from the group consisting of messenger RNA (mRNA), transfer RNA (tRNA), ribosomal RNA (rRNA), small interfering RNA (siRNA), microRNA (miRNA), short hairpin RNA (shRNA), small nuclear RNA (snRNA), and long noncoding RNA (lncRNA).
23. The method of alternative 21, wherein the nucleic acid of interest is a DNA aptamer or RNA aptamer.
24. A composition comprising a multivalent blocker comprising at least two negatively charged polymers or materials linked to a scaffold.
25. The composition of alternative 24, wherein the polymers linked to the scaffold are nucleic acids.
26. The composition of alternative 25, wherein at least one nucleic acid is selected from the group consisting of: a) a nucleic acid comprising a nucleotide sequence of (5'-TCGTGGAACTATCTAGCGGTGTACGT-GAGTGGGCATGTAGCAAGAGGGTC-3' (SEQ ID NO:1); and b) a nucleic acid comprising a nucleotide sequence having at least 81, 82, 83, 84, 85, 86, 87, 88, 89, 90, 91, 92, 93, 94, 95, 96, 97, 98, or 99% identity to the sequence of (5'-TCGTGGAAC-TATCTAGCGGTGTACGTGAGTGGG-CATGTAGCAAGAGGGTC-3' (SEQ ID NO:1).

27. The composition of anyone of alternatives 24-26, wherein 2-10 nucleic acids are linked to the scaffold.
28. The composition of anyone of alternatives 24-27, wherein 5 nucleic acids are linked to the scaffold.
29. The composition of anyone of alternatives 24-28, further comprising reagents for performing real time quantitative polymerase chain reaction (RT-PCR), microarray analysis, fluorescent in situ hybridization (FISH), a NanoString assay, next generation sequencing, fluorescence resonance energy transfer (FRET), T2 magnetic resonance (T2MR), antibody-detection by agglutination PCR (ADAP), or CRISPR-CAS9 genome editing, or transfection.
30. A kit comprising the composition of anyone of alternatives 24-29 and instructions for using a multivalent blocker for blocking non-specific interactions with nucleic acids in a sample.

These and other embodiments of the subject invention will readily occur to those of skill in the art in view of the disclosure herein.

DETAILED DESCRIPTION OF THE INVENTION

Figure 1:
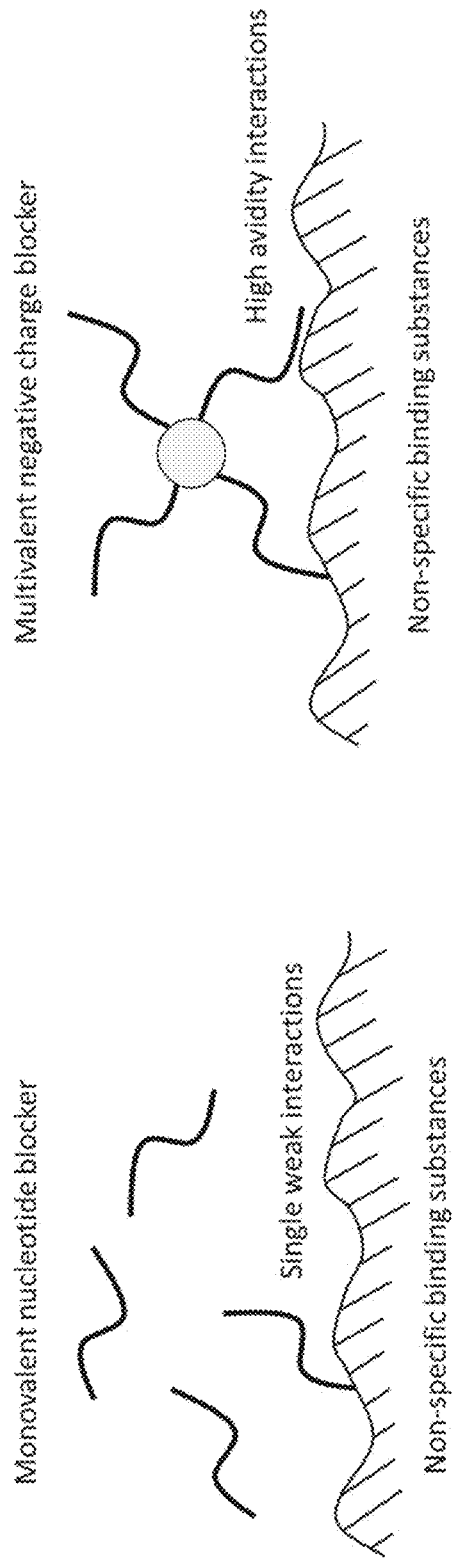
FIG. 1 shows that a traditional nucleic acid blocker could not bind non-specific binding substances with high enough avidity to eliminate non-specific binding. The multi-valent negative charge blocker could bind with much higher avidity, thereby efficiently shut down non-specific binding interactions. The core of multivalent blocker could be any materials that are capable of holding 2 or more nucleic acid together.

The practice of the present invention will employ, unless otherwise indicated, conventional methods of chemistry, biochemistry, molecular biology and recombinant DNA techniques, within the skill of the art. Such techniques are explained fully in the literature. See, e.g., *Nucleic Acid Detection: Methods and Protocols* (Methods in Molecular Biology, D. M. Kolpashchikov and Y. V. Gerasimova eds., Humana Press, 2013); *Handbook of Experimental Immunology*, Vols. I-IV (D. M. Weir and C. C. Blackwell eds., Blackwell Scientific Publications); T. E. Creighton, *Proteins: Structures and Molecular Properties* (W. H. Freeman and Company, 1993); A. L. Lehninger, *Biochemistry* (Worth Publishers, Inc., current addition); M. R. Green and J. Sambrook *Molecular Cloning: A Laboratory Manual* (Cold Spring Harbor Laboratory Press, 4th edition, 2012); *Methods In Enzymology* (S. Colowick and N. Kaplan eds., Academic Press, Inc.).

All publications, patents and patent applications cited herein, whether supra or infra, are hereby expressly incorporated by reference in their entireties.

1. Definitions

In describing the present invention, the following terms will be employed, and are intended to be defined as indicated below.

It must be noted that, as used in this specification and the appended claims, the singular forms "a." "an" and "the" include plural referents unless the content clearly dictates otherwise. Thus, for example, reference to "a nucleic acid" includes a mixture of two or nucleic acids, and the like.

The term "about." particularly in reference to a given quantity, is meant to encompass deviations of plus or minus five percent.

The terms "polynucleotide." "oligonucleotide," "nucleic acid" and "nucleic acid molecule" are used herein to include a polymeric form of nucleotides of any length, either ribonucleotides or deoxyribonucleotides. This term refers only to the primary structure of the molecule. Thus, the term includes triple-, double- and single-stranded DNA, as well as triple-, double- and single-stranded RNA. It also includes modifications, such as by methylation and/or by capping, and unmodified forms of the polynucleotide. More particularly, the terms "polynucleotide," "oligonucleotide," "nucleic acid" and "nucleic acid molecule" include polydeoxyribonucleotides (containing 2-deoxy-D-ribose), polyribonucleotides (containing D-ribose), any other type of polynucleotide which is an N- or C-glycoside of a purine or pyrimidine base, and other polymers containing nonnucleotidic backbones, for example, polyamide (e.g., peptide nucleic acids (PNAs)) and polymorpholino (commercially available from the Anti-Virals, Inc., Corvallis, Oregon, as Neugene) polymers, and other synthetic sequence-specific nucleic acid polymers providing that the polymers contain nucleobases in a configuration which allows for base pairing and base stacking, such as is found in DNA and RNA. There is no intended distinction in length between the terms "polynucleotide," "oligonucleotide," "nucleic acid" and "nucleic acid molecule," and these terms will be used interchangeably. Thus, these terms include, for example, 3'-deoxy-2',5'-DNA, oligodeoxyribonucleotide N3' P5' phosphoramidates, 2'-O-alkyl-substituted RNA, double- and single-stranded DNA, as well as double- and single-stranded RNA, DNA:RNA hybrids, and hybrids between PNAs and DNA or RNA, and also include known types of modifications, for example, labels which are known in the art, methylation, "caps," substitution of one or more of the naturally occurring nucleotides with an analog, internucleotide modifications such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalklyphosphoramidates, aminoalkylphosphotriesters), those containing pendant moieties, such as, for example, proteins (including nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide.

"Recombinant" as used herein to describe a nucleic acid molecule means a polynucleotide of genomic, cDNA, viral, semisynthetic, or synthetic origin which, by virtue of its origin or manipulation is not associated with all or a portion of the polynucleotide with which it is associated in nature. The term "recombinant" as used with respect to a protein or polypeptide means a polypeptide produced by expression of a recombinant polynucleotide. In general, the gene of interest is cloned and then expressed in transformed organisms, as described further below. The host organism expresses the foreign gene to produce the protein under expression conditions.

As used herein, the term "binding pair" refers to first and second molecules that specifically bind to each other, such as a ligand and a receptor, an antigen and an antibody, or biotin and streptavidin. "Specific binding" of the first member of the binding pair to the second member of the binding pair in a sample is evidenced by the binding of the first member to the second member, or vice versa, with greater affinity and specificity than to other components in the sample. The binding between the members of the binding pair is typically noncovalent.

As used herein, a "solid support" refers to a solid surface such as a magnetic bead, non-magnetic bead, microtiter plate well, glass plate, nylon, agarose, acrylamide, and the like.

"Substantially purified" generally refers to isolation of a substance (compound, polynucleotide, protein, polypeptide, peptide composition) such that the substance comprises the majority percent of the sample in which it resides. Typically, in a sample, a substantially purified component comprises 50%, preferably 80%-85%, more preferably 90-95% of the sample. Techniques for purifying polynucleotides and polypeptides of interest are well-known in the art and include, for example, ion-exchange chromatography, affinity chromatography and sedimentation according to density.

By "isolated" is meant, when referring to a protein, polypeptide or peptide, that the indicated molecule is separate and discrete from the whole organism with which the molecule is found in nature or is present in the substantial absence of other biological macro molecules of the same type. The term "isolated" with respect to a nucleic acid is a nucleic acid molecule devoid, in whole or part, of sequences normally associated with it in nature; or a sequence, as it exists in nature, but having heterologous sequences in association therewith; or a molecule disassociated from the chromosome.

As used herein, the term "probe" or "oligonucleotide probe" refers to a polynucleotide, as defined above, that contains a nucleic acid sequence complementary to a nucleic acid sequence present in the target nucleic acid analyte. The polynucleotide regions of probes may be composed of DNA, and/or RNA, and/or synthetic nucleotide analogs. Probes may be labeled in order to detect the target sequence. Such a label may be present at the 5' end, at the 3' end, at both the 5' and 3' ends, and/or internally. The "oligonucleotide probe" may contain at least one fluorescer and at least one quencher. Quenching of fluorophore fluorescence may be eliminated by exonuclease cleavage of the fluorophore from the oligonucleotide (e.g., TaqMan assay) or by hybridization of the oligonucleotide probe to the nucleic acid target sequence (e.g., molecular beacons). Additionally, the oligonucleotide probe will typically be derived from a sequence that lies between the sense and the antisense primers when used in a nucleic acid amplification assay.

The terms "hybridize" and "hybridization" refer to the formation of complexes between nucleotide sequences which are sufficiently complementary to form complexes via Watson-Crick base pairing. Where a primer "hybridizes" with target (template), such complexes (or hybrids) are sufficiently stable to serve the priming function required by, e.g., the DNA polymerase to initiate DNA synthesis.

It will be appreciated that the hybridizing sequences need not have perfect complementarity to provide stable hybrids. In many situations, stable hybrids will form where fewer than about 10% of the bases are mismatches, ignoring loops of four or more nucleotides. Accordingly, as used herein the term "complementary" refers to an oligonucleotide that forms a stable duplex with its "complement" under assay conditions, generally where there is about 90% or greater homology.

The term "antibody" encompasses polyclonal and monoclonal antibody preparations, as well as preparations including hybrid antibodies, altered antibodies, chimeric antibodies and, humanized antibodies, as well as: hybrid (chimeric) antibody molecules (see, for example, Winter et al. (1991) *Nature* 349:293-299; and U.S. Pat. No. 4,816,567); F(ab') 2 and F (ab) fragments; Fv molecules (noncovalent heterodimers, see, for example, Inbar et al. (1972) *Proc Natl Acad Sci USA* 69:2659-2662; and Ehrlich et al. (1980) *Biochem* 19:4091-4096); single-chain Fv molecules (sFv) (see, e.g., Huston et al. (1988) *Proc Natl Acad Sci USA* 85:5879-5883); nanobodies or single-domain antibodies (sdAb) (see, e.g., Wang et al. (2016) *Int J Nanomedicine* 11:3287-3303, Vincke et al. (2012) *Methods Mol Biol* 911:15-26; dimeric and trimeric antibody fragment constructs; minibodies (see, e.g., Pack et al. (1992) *Biochem* 31:1579-1584; Cumber et al. (1992) *J Immunology* 149B: 120-126); humanized antibody molecules (see, e.g., Riechmann et al. (1988) *Nature* 332:323-327; Verhocyan et al. (1988) *Science* 239:1534-1536; and U.K. Patent Publication No. GB 2,276,169, published 21 Sep. 1994); and, any functional fragments obtained from such molecules, wherein such fragments retain specific-binding properties of the parent antibody molecule.

The phrase "specifically (or selectively) binds" to an antibody or "specifically (or selectively) immunoreactive with," when referring to an antigen or allergen, refers to a binding reaction that is determinative of the presence of the antigen or allergen in a heterogeneous population of proteins and other biologics. Thus, under designated immunoassay conditions, the specified antibodies bind to a particular antigen at least two times the background and do not substantially bind in a significant amount to other antigens present in the sample. Specific binding to an antibody under such conditions may require an antibody that is selected for its specificity for a particular antigen. For example, polyclonal antibodies raised to an antigen from specific species such as rat, mouse, or human can be selected to obtain only those polyclonal antibodies that are specifically immunoreactive with the antigen and not with other proteins, except for polymorphic variants and alleles. This selection may be achieved by subtracting out antibodies that cross-react with molecules from other species. A variety of immunoassay formats may be used to select antibodies specifically immunoreactive with a particular antigen. For example, solid-phase ELISA immunoassays are routinely used to select antibodies specifically immunoreactive with a protein (see, e.g., Harlow & Lane. Antibodies, A Laboratory Manual (1988), for a description of immunoassay formats and conditions that can be used to determine specific immunoreactivity). Typically, a specific or selective reaction will be at least twice background signal or noise and more typically more than 10 to 100 times background.

As used herein, a "biological sample" refers to a sample of cells, tissue, or fluid isolated from a subject, including but not limited to, for example, blood, plasma, serum, fecal matter, urine, bone marrow, bile, spinal fluid, lymph fluid, samples of the skin, external secretions of the skin, respiratory, intestinal, and genitourinary tracts, tears, saliva, milk, cells (e.g., epithelial and endothelial cells, fibroblasts, and macrophages), muscles, joints, organs (e.g., liver, lung, spleen, thymus, kidney, brain, or lymph node), biopsies and also samples of in vitro cell culture constituents including but not limited to conditioned media resulting from the growth of cells and tissues in culture medium, e.g., recombinant cells, and cell components.

As used herein, the terms "label" and "detectable label" refer to a molecule capable of detection, including, but not limited to, radioactive isotopes, fluorescers, chemiluminescers, chromophores, enzymes, enzyme substrates, enzyme cofactors, enzyme inhibitors, semiconductor nanoparticles, dyes, metal ions, metal sols, ligands (e.g., biotin, strepavidin or haptens) and the like. The term "fluorescer" refers to a substance or a portion thereof which is capable of exhibiting fluorescence in the detectable range. Particular examples of labels which may be used in the practice of the invention include, but are not limited to, SYBR green, SYBR gold, a CAL Fluor dye such as CAL Fluor Gold 540, CAL Fluor Orange 560, CAL Fluor Red 590, CAL Fluor Red 610, and CAL Fluor Red 635, a Quasar dye such as Quasar 570, Quasar 670, and Quasar 705, an Alexa Fluor such as Alexa Fluor 350, Alexa Fluor 488, Alexa Fluor 546, Alexa Fluor 555, Alexa Fluor 594, Alexa Fluor 647, and Alexa Fluor 784, a cyanine dye such as Cy 3, Cy3.5, Cy5, Cy5.5, and Cy7, fluorescein, 2', 4', 5', 7'-tetrachloro-4-7-dichlorofluorescein (TET), carboxyfluorescein (FAM), 6-carboxy-4',5'-dichloro-2',7'-dimethoxyfluorescein (JOE), hexachlorofluorescein (HEX), rhodamine, carboxy-Xrhodamine (ROX), tetramethyl rhodamine (TAMRA), FITC, dansyl, umbelliferone, dimethyl acridinium ester (DMAE), Texas red, luminol, NADPH, horseradish peroxidase (HRP), and α-β-galactosidase.

2. Modes of Carrying Out the Invention

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of methods and materials similar or equivalent to those described herein can be used in the practice of the present invention, the preferred materials and methods are described herein.

The present invention is based on the discovery of reagents and methods for blocking non-specific interactions with nucleic acids. The inventors have shown that multivalent blockers comprising at least two negatively charged polymers linked to a scaffold are effective in blocking non-specific interactions with nucleic acids in a sample (Example 1). In particular, the inventors designed multivalent blockers comprising multiple (2 or more) nucleic acids or negatively charged acrylic acid polymers linked to scaffolds made up of dendrimers, streptavidin, or gold nanoparticles and showed that such multivalent blockers were significantly more effective in blocking non-specific interactions with nucleic acids than single-stranded or double-stranded nucleic acids commonly used as blocking agents (Example 1).

In order to further an understanding of the invention, a more detailed discussion is provided below regarding such multivalent blockers and their use in various applications for reducing interference from non-specific interactions with nucleic acids.

A. Multivalent Blockers

Multivalent blockers for blocking non-specific interactions with nucleic acids comprise at least two negatively charged polymers linked to a scaffold. Such multivalent blockers bind to positively charged compounds or materials in a sample, thereby blocking non-specific interactions with nucleic acids of interest. The multivalent blockers of the invention will find use with various nucleic acid-based techniques to reduce undesired nonspecific interactions with nucleic acids.

The scaffold in the multivalent blocker provides a structure upon which the negatively charged polymers can associate or attach. Scaffolds may have a variety of geometric shapes, including spherical (e.g., beads, pellets), nonspherical (e.g., non-spherical nano- and micro-scale particles), linear (e.g., linear polymers or fibers), branched (e.g. 2 or more branches with binding sites for negatively charge polymers), or planar (e.g., thin sheet, membrane, or plate). Exemplary scaffold materials include dendrimers (e.g., PAMAM), multi-armed polyethylene glycol (PEG), metal nanoparticles (e.g., nanoparticles comprising biocompatible metals such as gold, silver palladium, platinum, or titanium, or metal alloys or oxides thereof), or proteins (e.g., streptavidin). Additionally, a coating may be added to the surface of a scaffold to facilitate attachment of negatively charged polymers to the surface.

In certain embodiments, the scaffold comprises a dendrimer. Dendrimers are symmetric, spherical, highly branched compounds made up of a series of branches extending from an inner core. The compounds are classified by generation, which refers to the number of branching synthesis cycles that are performed to produce them. Dendrimers of higher generation have more cycles of branching and higher molecular weights. A variety of dendrimers are suitable for use as scaffolds in multivalent blockers, including, but not limited to, polylysine, poly(amidoamine) (PAMAM), poly(propylene imine) (PPI or DAB), and poly(etherhydroxylamine) (PEHAM) dendrimers of various generations. For a description of dendrimers and methods of synthesizing and conjugating them, see, e.g., *Dendrimers and Other Dendritic Polymers* (Wiley Series in Polymer Science, J. M. J. Fréchet and D. A. Tomalia eds., Wiley, 2002), *Dendrimers* (Topics in Current Chemistry, Fritz Vogtle ed., Springer, 1998), *Dendrimers: Synthesis, Applications and Role in Nanotechnology* (Chemical Engineering Methods and Technology, H. B. Harris and B. L. Turner eds., Nova Science Pub Inc. 2013), Kalhapure et al. (2015) Pharm. Dev. Technol. 20 (1): 22-40, Sato et al. (2013) Molecules. 18 (7): 8440-8460, Lallana et al. (2012) Pharm. Res. 29 (4): 902-921, Caminade et al. (2012) Molecules 17 (11): 13605-21, Wang et al. (2012) Curr. Med. Chem. 19 (29): 5011-5028, Arsencault et al. (2015) Molecules 20 (5): 9263-9294, Walter et al. (2012) Chem. Soc. Rev. 41 (13): 4593-4609, and Najlah et al. (2007) Curr. Opin. Drug Discov. Devel. 10 (6): 756-767; herein incorporated by reference. Dendrimers are commercially available from a number of companies, including Sigma-Aldrich (St. Louis, MO), Dendritech (Midland, MI), Starpharma (Melbourne, Australia), Polymer Factory (Stockholm, Sweden), and TCI Chemicals (Portland, OR).

Negatively charged polymers that can be linked to the scaffold include, but are not limited to, negatively charged nucleic acids (e.g., DNA or RNA), peptides, polysaccharides, and poly(acrylic acid) polymers. The polymers linked to the scaffold, for example, may comprise one or more negatively charged functional groups such as, but not limited to, carboxylate, sulfate, and phosphate groups. In certain embodiments, 2-10 or more negatively charged polymers may be linked to the scaffold, including any number of negatively charged polymers in this range, such as 1, 2, 3, 4, 5, 6, 7, 8, 9, 10, or more negatively charged polymers.

In certain embodiments, nucleic acids (e.g., DNA or RNA) are attached to the scaffold. Generally, the length of the nucleic acids attached to the scaffold will be at least 10 nucleotides, but may range from 10 nucleotides to 200 nucleotides or more including but not limited to e.g., 10 or more nucleotides, 20 or more nucleotides, 25 or more nucleotides, 30 or more nucleotides, 35 or more nucleotides, 40 or more nucleotides, 45 or more nucleotides, 50 or more nucleotides, 55 or more nucleotides, 60 or more nucleotides, 65 or more nucleotides, 70 or more nucleotides, 75 or more nucleotides, 80 or more nucleotides, 90 or more nucleotides, 95 or more nucleotides, 100 or more nucleotides, 10 to 1000 nucleotides, 15 to 200 nucleotides, 20 to 200 nucleotides, 25 to 200 nucleotides, 30 to 200 nucleotides, 35 to 200 nucleotides, 40 to 200 nucleotides, 45 to 200 nucleotides, 50 to 200 nucleotides, 15 to 100 nucleotides, 20 to 100 nucleotides, 25 to 100 nucleotides, 30 to 100 nucleotides, 35 to 100 nucleotides, 40 to 100 nucleotides, 45 to 100 nucleotides, 50 to 100 nucleotides, 10 to 60 nucleotides, or 15 to 50 nucleotides, including any number of nucleotides in these ranges such as 10, 15, 20, 25, 30, 35, 40, 41, 42, 43, 44, 45, 46, 47, 48, 49, 50, 51, 52, 53, 54, 55, 56, 57, 57, 59, 60, 65, 70, 75, 80, 85, 90, 95, 100, 120, 140, 160, 180, 200, 400, 600, 800, or 1000 nucleotides. Exemplary multivalent blockers having 2 to 10 nucleic acids attached to a scaffold, are described in Example 1. In certain embodiments, at least one nucleic acid attached to the scaffold comprises a nucleotide sequence of (5'-TCGTGGAACTATCTAGCGGTGTACGTGAGTGGG-CATGTAGCAAGAGGGTC-3' (SEQ ID NO: 1) or a nucleotide sequence displaying at least about 80-100% sequence identity thereto, including any percent identity within this range, such as 81, 82, 83, 84, 85, 86, 87, 88, 89, 90, 91, 92, 93, 94, 95, 96, 97, 98, 99% sequence identity thereto, wherein the multivalent blocker is capable of blocking non-specific interactions with a nucleic acid of interest in a sample.

Nucleic acids (e.g., DNA or RNA) may be attached to a scaffold by any convenient method, as described in more detail below. The nucleic acids may be attached to a scaffold at any convenient point along the length of the nucleic acid, including at the 3' or 5' termini. In some instances, a nucleic acid is attached to the scaffold at its 3' end or 5' end. In some instances, all nucleic acid molecules are attached at their 3' ends to the scaffold. In some instances, all nucleic acids are attached at their 5' ends to the scaffold.

In other embodiments, negatively charged polysaccharides are linked to a scaffold. Negatively charged polysaccharides may include those with carboxylate groups (e.g. pectin, alginate, hyaluronan, or carboxymethylcellulose) or sulfate groups (e.g. carrageenan, heparin, or dextran sulfate). In addition, neutral polysaccharides can be chemically modified with anionic groups to make them negatively charged (e.g., carboxymethylation of pullulan or dextran, sulfation of pullulan or glucuronan).

In yet other embodiments, negatively charged peptides are linked to a scaffold. Peptides may have an overall negative charge due to the presence of carboxylate groups from aspartate or glutamate residues. In addition, peptides may be modified chemically or enzymatically to add negatively charged groups to amino acids (e.g., serine, threonine, or tyrosine phosphorylation by a kinase or tyrosine sulfation by a sulfotransferase).

Negatively charged polymers can be "linked," "conjugated," or "attached" to or "associated" with the scaffold either covalently or noncovalently. Crosslinking agents that can be used for covalently attaching negatively charged polymers to a scaffold include, but are not limited to, dimethyl suberimidate, N-hydroxysuccinimide, formaldehyde, and glutaraldehyde. In addition, carboxyl-reactive chemical groups such as diazomethane, diazoacetyl, and carbodiimide can be included for crosslinking carboxylic acids to primary amines. In particular, the carbodiimide compounds, 1-ethyl-3-(−3-dimethylaminopropyl) carbodiimide hydrochloride (EDC) and N',N'-dicyclohexyl carbodiimide (DCC) can be used for conjugation with carboxylic acids. In order to improve the efficiency of crosslinking reactions, N-hydroxysuccinimide (NHS) or a water-soluble analog (e.g., Sulfo-NHS) may be used in combination with a carbodiimide compound. The carbodiimide compound (e.g., EDC or DCC) couples NHS to carboxyl groups to form an NHS ester intermediate, which readily reacts with primary amines at physiological pH. In addition, ultraviolet light can be used for linking negatively charged polymers to a scaffold. For a description of various crosslinking agents and techniques, see, e.g., Wong and Jameson *Chemistry of Protein and Nucleic Acid Cross-Linking and Conjugation* (CRC Press, 2nd edition, 2011), Hermanson Bioconjugate Techniques (Academic Press, 3rd edition, 2013), herein incorporated by reference in their entireties.

In certain embodiments, linking of negatively charged polymers to a scaffold is performed using click chemistry. Click chemistry can be performed with suitable crosslinking agents comprising reactive azide or alkyne functional groups. See, e.g., Kolb et al., 2004, Angew Chem. Int. Ed. 40:3004-31; Evans, 2007, Aust. J. Chem. 60:384-95; Millward et al. (2013) Integr. Biol. (Camb) 5 (1): 87-95), Lallana et al. (2012) Pharm. Res. 29 (1): 1-34, Gregoritza et al. (2015) Eur. J. Pharm. Biopharm. 97 (Pt B): 438-453, Musumeci et al. (2015) Curr. Med. Chem. 22 (17): 2022-2050, Mckay et al. (2014) Chem. Biol. 21 (9): 1075-1101, Ulrich et al. (2014) Chemistry 20 (1): 34-41, Pasini (2013) Molecules 18 (8): 9512-9530, and Wangler et al. (2010) Curr. Med. Chem. 17 (11): 1092-1116; herein incorporated by reference in their entireties.

In particular, crosslinking can be performed using strain-promoted azide-alkyne cycloaddition (SPAAC) click chemistry, a Cu-free variation of click chemistry. SPAAC utilizes a substituted cyclooctyne having an internal alkyne in a strained ring system. Ring strain together with electron-withdrawing substituents in the cyclooctyne promote a [3+2] dipolar cycloaddition with an azide functional group. SPAAC can be used for bioconjugation and crosslinking by attaching azide and cyclooctyne moieties to molecules. For a description of SPAAC, see, e.g., Baskin et al. (2007) Proc. Natl. Acad. Sci. USA 104 (43): 16793-16797. Agard et al. (2006) ACS Chem. Biol. 1:644-648, Codelli et al. (2008) J. Am. Chem. Soc. 130:11486-11493, Gordon et al. (2012) J. Am. Chem. Soc. 134:9199-9208, Jiang et al. (2015) Soft Matter 11 (30): 6029-6036, Jang et al. (2012) Bioconjug Chem. 23 (11): 2256-2261, Ornelas et al. (2010) J. Am. Chem. Soc. 132 (11): 3923-3931; herein incorporated by reference in their entireties.

In other embodiments, the negatively charged polymer and scaffold are noncovalently linked together. For example, scaffolds with cationic groups can bind negatively charged polymers noncovalently through electrostatic interactions. Alternatively, the negatively charged polymer and/or scaffold can be conjugated to a specific-binding molecule or member of a binding pair to allow association of the polymer and scaffold through noncovalent binding interactions in a complex. A "binding pair" refers to first and second molecules that specifically bind to each other, such as a ligand, hormone, antagonist, or agonist and a receptor, an antigen, epitope, hapten and an antibody, or biotin and a biotin-binding protein such as streptavidin or avidin. For example, a negatively charged polymer can be biotinylated to allow noncovalent association of the polymer with a scaffold comprising a biotin-binding protein such as streptavidin or avidin. In another example, the negatively charged polymer is modified to add an epitope (e.g., conjugated to an antigen or hapten) to allow noncovalent association of the polymer with a scaffold comprising an antibody. In yet another example, the negatively charged polymer is conjugated to a ligand to allow noncovalent association of the polymer with a scaffold comprising a receptor.

B. Applications

The multivalent blockers described herein are useful for blocking nonspecific interactions with nucleic acids and may find use in various applications that utilize nucleic acid materials. Multivalent blockers may be used for blocking nonspecific interactions with any type of nucleic acid, including DNA or RNA. For example, a multivalent blocker can be used to block nonspecific interactions with any type of RNA molecule such as, but not limited to, messenger RNA (mRNA), transfer RNA (tRNA), ribosomal RNA (rRNA), small interfering RNA (siRNA), microRNA (miRNA), short hairpin RNA (shRNA), small nuclear RNA (snRNA), and long noncoding RNA (lncRNA). In another example, the nucleic acid of interest is a DNA aptamer or RNA aptamer.

Multivalent blockers can be used to block nonspecific interactions in assays that require nucleic acid binding to a target such as assays using aptamers (e.g. Somalogic assays), or assays requiring nucleic acid hybridization such as assays using PCR, DNA/RNA microarrays, fluorescent in situ hybridization (FISH), NanoString assays, or next generation sequencing. Multivalent blockers can also be used in assays that require proximity of two nucleic acid probes, such as FRET, T2MR, and antibody-detection by agglutination PCR (ADAP) assays. In addition, multivalent blockers can be used in any assay that uses nucleic acid labeled agents such as nucleic acid-antibody conjugates or nucleic acid-antigen conjugates (e.g., immuno-PCR) or other nucleic acid labeled cargos. Moreover, multivalent blockers can be used in any assays requiring the introduction of nucleic acid reagents to a specific site such as transfection, siRNA, microRNA, CRISPR-CAS9 genome editing, and aptamer blocking.

C. Kits

The multivalent blockers described herein may be included in kits with suitable instructions for blocking non-specific interactions with nucleic acids of interest. In addition, kits may further include sample preparation reagents, transfection agents, detection reagents (e.g., probes), reagents useful in amplification (e.g., PCR reagents and/or isothermal amplification reagents and/or qPCR reagents, etc.), sequencing, or performing assays (fluorescent in situ hybridization (FISH), a NanoString assay, fluorescence resonance energy transfer (FRET), T2MR. ADAP) or genome editing with nucleic acids (e.g., CRISPR-CAS9 genome editing), buffers, diluents, etc.

The kit can comprise one or more containers for compositions contained in the kit. The kit will normally contain in separate containers the different agents, including multivalent blockers and other reagents. Compositions can be in liquid form or can be lyophilized. Suitable containers for the compositions include, for example, bottles, vials, syringes, and test tubes. Containers can be formed from a variety of materials, including glass or plastic. Instructions (e.g., written, CD-ROM, DVD, Blu-ray, flash drive, digital download, etc.) for blocking non-specific interactions with nucleic acids will also usually be included in the kit.

In certain embodiments, the multivalent blocker in the kit comprises 2-10 or more negatively charged polymers linked to a scaffold, including any number of negatively charged polymers in this range, such as 1, 2, 3, 4, 5, 6, 7, 8, 9, 10, or more negatively charged polymers. The polymers linked to the scaffold, for example, may comprise one or more negatively charged functional groups such as, but not limited to, carboxylate, sulfate, and phosphate groups. The negatively charged polymers can be linked to the scaffold covalently or noncovalently.

In certain embodiments, the polymers linked to the scaffold are nucleic acids. For example, 2-10 or more nucleic acids may be linked to the scaffold, including any number of nucleic acids in this range, such as 1, 2, 3, 4, 5, 6, 7, 8, 9, 10, or more nucleic acids. In certain embodiments, the kit comprises a multivalent blocker comprising at least two nucleic acids linked to a scaffold, wherein at least one nucleic acid comprises the nucleotide sequence of (5'-TCGTGGAACTATCTAGCGGTGTACGTGAGTGGG-CATGTAGCAAGAGGGTC-3' (SEQ ID NO:1), or a sequence displaying at least about 80-100% sequence identity thereto, including any percent identity within this range, such as 81, 82, 83, 84, 85, 86, 87, 88, 89, 90, 91, 92, 93, 94, 95, 96, 97, 98, 99% sequence identity thereto, wherein the multivalent blocker is capable of blocking non-specific interactions with a nucleic acid of interest in a sample.

In other embodiments the polymers linked to the scaffold are negatively charged polymers, such as poly(acrylic acid) polymers. For example, 2-10 or more negatively charged polymers may be linked to the scaffold, including any number of negatively charged polymers in this range, such as 1, 2, 3, 4, 5, 6, 7, 8, 9, 10, or more negatively charged polymers.

In certain embodiments, the kit comprises a multivalent blocker comprising a scaffold comprising a dendrimer (e.g., polyamidoamine (PAMAM) dendrimer), a multi-armed polyethylene glycol (PEG), a nanoparticle (e.g., gold nanoparticle), or a protein (e.g., streptavidin or avidin).

In another embodiment, the kit further comprises one or more reagents for performing real time quantitative PCR, microarray analysis, fluorescent in situ hybridization (FISH), a NanoString assay, next generation sequencing, fluorescence resonance energy transfer (FRET), T2 magnetic resonance (T2MR), antibody-detection by agglutination PCR (ADAP), or CRISPR-CAS9 genome editing, or transfection.

3. Experimental

This section provides greater detail on desirable embodiments for carrying out the present invention.

Efforts have been made to ensure accuracy with respect to numbers used (e.g., amounts, temperatures, etc.), but some experimental error and deviation should, of course, be allowed for.

Blocking Non-Specific Interactions with Nucleic Acids

Description of invention: Several common biological compounds are known to facilitate unwanted interactions with nucleic acids. These substances include fibrinogen, fibrin degradation product, cell debris including nucleoproteins and histones [11]. Many of these molecules are positive charged, permitted electrostatic interaction with negatively charged nucleic acids. Reported binding constants between these substances and nucleic acids vary widely. In addition, these substances can exist in biological samples in wide concentration ranges (pM to mM). Lab plastics also adsorb nucleic acid molecules, facilitating non-specific interactions and sequestration. A universal blocking agent ideally should neutralize all these types of interfering compounds.

Currently-used blocking materials fail to neutralize all potential sites of non-specific binding. Thus, functional and useful nucleic acids are still vulnerable to nonspecifically bind with interfering substances. We hypothesized that the failure of state of the art blocking agents is caused by their limited affinity for the non-specifically binding substances. A state of the art blocker may engage with non-specific binding sites temporarily, then dissociate, and re-associate. However, during the period when blocking agents dissociate, precious nucleic acid materials may be bound at non-specific binding sites.

Figure 2:
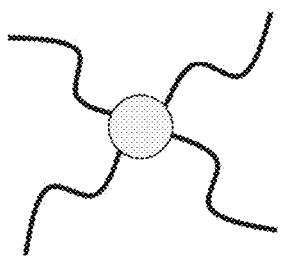
FIG. 2 shows that the multivalent negative charge blocker could use nucleic acid (e.g. DNA, RNA) as the negative charge source. Alternatively, it could also use other negative charge polymer as a negative charge sources such as poly-acrylic acid.
Figure 2:
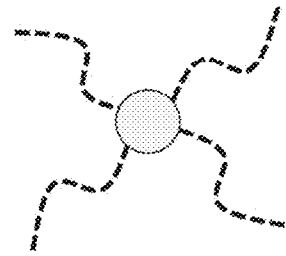

Here we describe a substantially improved method to block and prevent nonspecific interactions between nucleic acids and other molecules, and provide experimental evidence showing that our method is more effective than other current methods. We invented a highly potent nucleic acid blocking agent that engages with non-specific binding sites with substantially enhanced avidity, thereby reducing the possibility of dissociation from the non-specific binding sites (FIGS. 1 and 2).

Our blocking agent is a multi-valent nucleic acid material, which is produced by linking two or more nucleic acids onto a common scaffold. We demonstrated the scaffold could be organic molecules (such as a dendrimer), inorganic molecules (nanoparticles), or biological molecules (such as streptavidin). We also demonstrated the linkage between the nucleic acid and the scaffold could be either covalent or non-covalent. We demonstrate the multi-valency alone is the major critical factor in enhancing blocking efficacy. Taken together, this invention employs multi-valent nucleic acids as a new generation of blocking agents to permanently and completely engage charged surfaces of interfering species, thereby eliminating non-specific interactions.

Alternatively, negatively charged polymers can be used in synthesis of a multivalent blocker that has two or more arms of negative charges. This type of multi-valent blocker should also be able to engage with non-specific nucleic acid binding sites with high avidity (FIG. 2).

Indeed, multi-valency is a common molecular strategy to increase binding affinity between proteins. For instance, a monovalent major histocompatibility complex (MHC)-peptide complex only weakly interacts with the T-cell receptor, making it difficult to for labeling or imaging. By assembling biotinylated MHC-peptide complexes into a tetramer through the use of streptavidin, the interaction of the tetrameric ensemble with T-cell receptors is greatly enhanced, permitting labeling for further experiments [10].

Our multi-valent nucleic acid blocker is inspired by the aforementioned example. We hypothesized and validated with evidence described below that multi-valent nucleic acid materials could be used to boost binding avidity with non-specific nucleic acid binding sites, thus achieving much improved reduction of non-specific binding in comparison to current state of the art methods.

Evidence: To assure our multi-valent nucleic acid blocker indeed blocks nonspecific interactions and improves performance in comparison to state of the art methods, we tested their impact in a nucleic acid-based immunoassay, termed antibody-detection by agglutination-PCR (ADAP) assay [5]. In this assay, antigen-DNA conjugates probes are used to detect presence of target antibodies in a biological specimen. Here, we used green fluorescent protein (GFP)-DNA conjugates as negative control probes. As human samples should not contain antibodies against GFP, we expect that all human samples should generate signal very close to the baseline (or hopefully no signals at all). However, when assaying large batches of human samples, we consistently identified samples that generated strong signals in the presumed absence of anti-GFP antibodies. These results indicated the presence of non-specific nucleic acid interactions.

Figure 6:
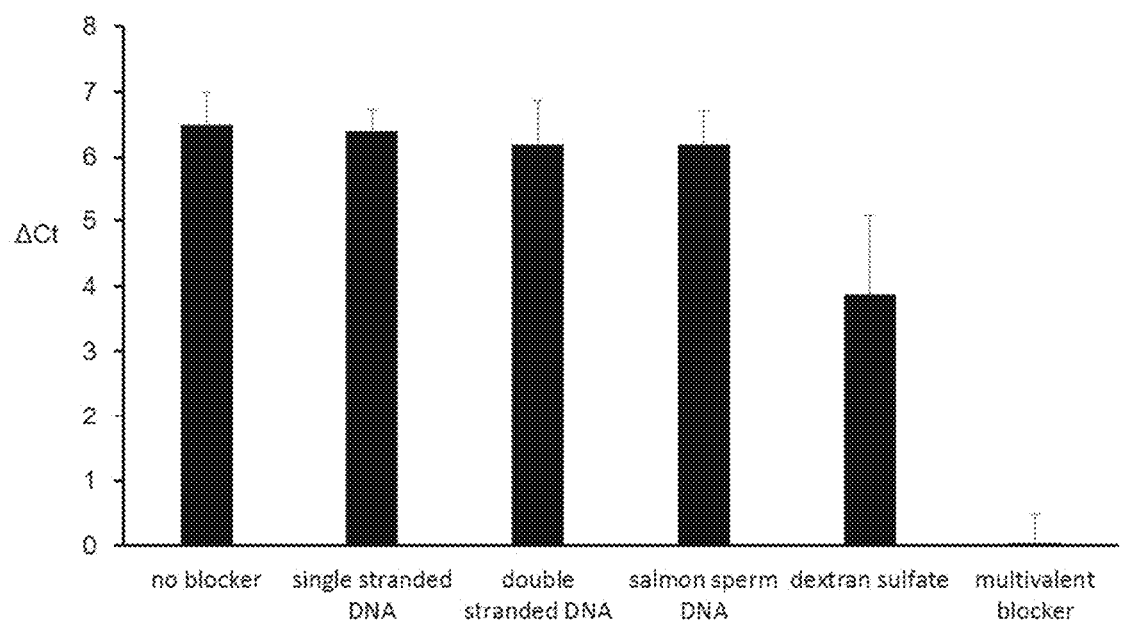
FIG. 6 shows tests for blocking the efficiency of various blockers. The data demonstrated multivalent blocker completely eliminated non-specific background signals when assaying patient serum containing interfering substances.

To identify blocking agent that could reduce the background signals, we first used blocking agents such as synthetic single-stranded DNA (60 bp) at very high quantity (10 mg/mL). However, no improvement of background signals was observed. Similarly, the addition of extracted salmon sperm DNA at high concentration (5 mg/mL) does not reduce the background. In contrast, with the addition of a multi-valent single-stranded DNA blocker, we saw complete elimination of background signals, suggesting that this material has drastically improved blocking properties compared to state of the art methods (FIG. 6).

Figure 5:
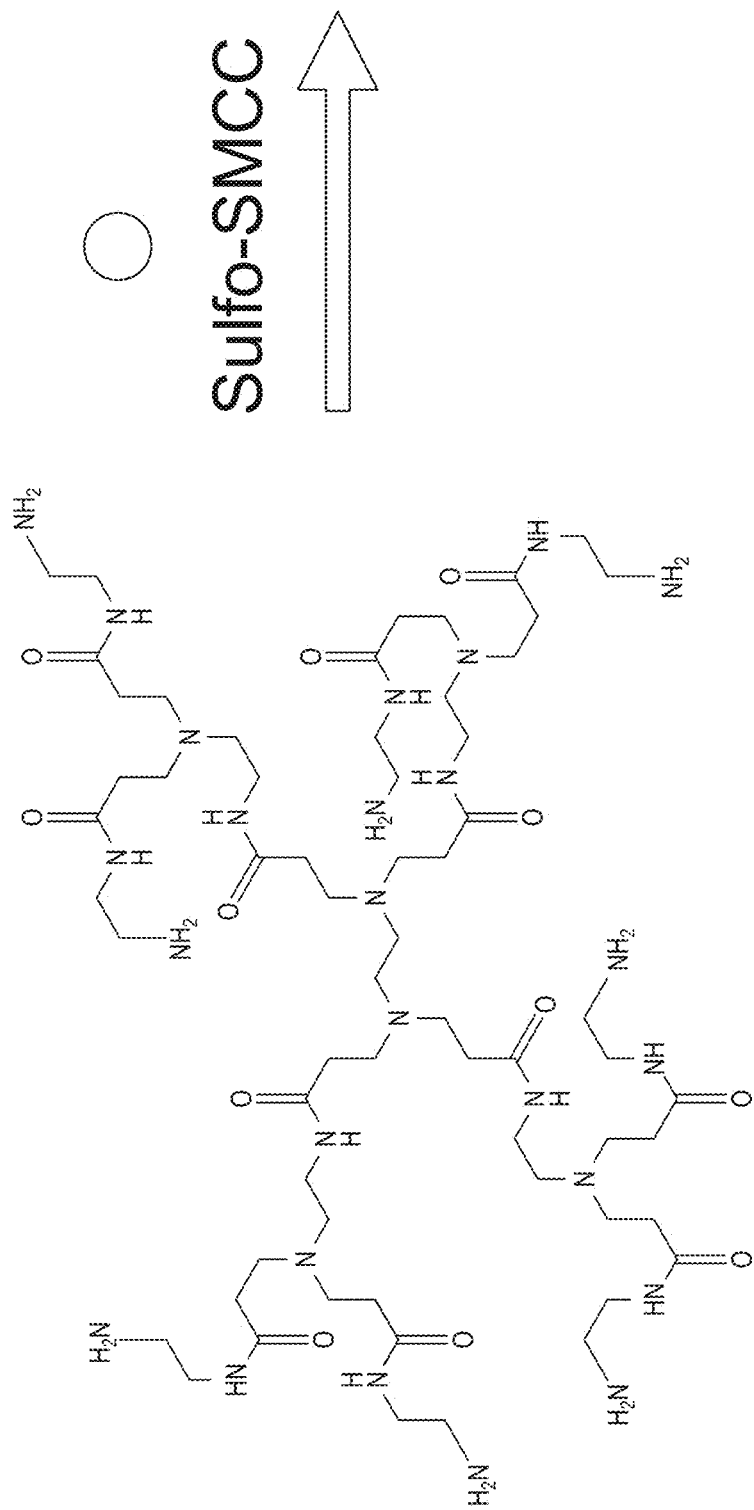
FIG. 5 shows that the multivalent nucleic acid blocker can be synthesized by conjugating a thiolated nucleic acid onto a dendrimer scaffold.
Figure 5:
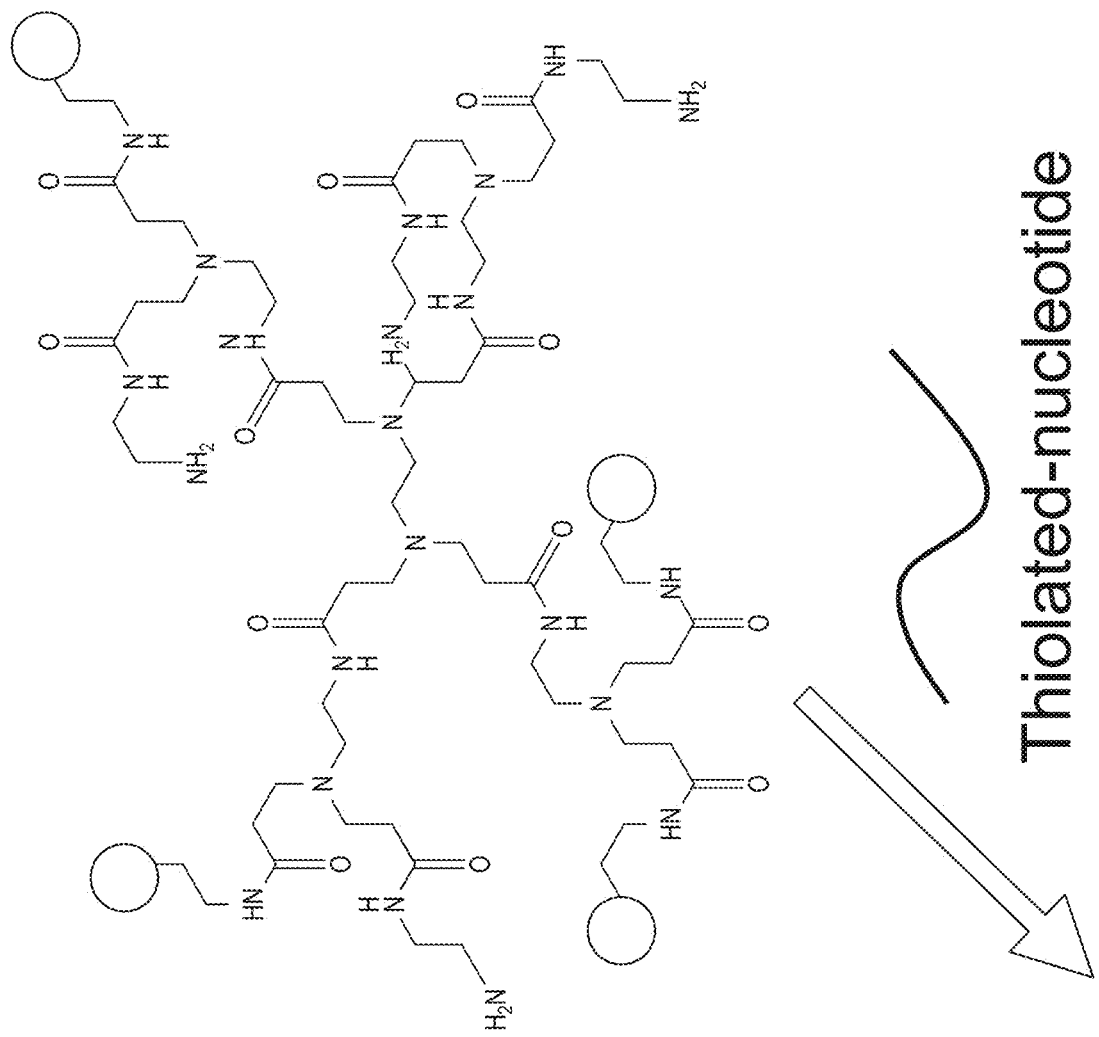
Figure 5:
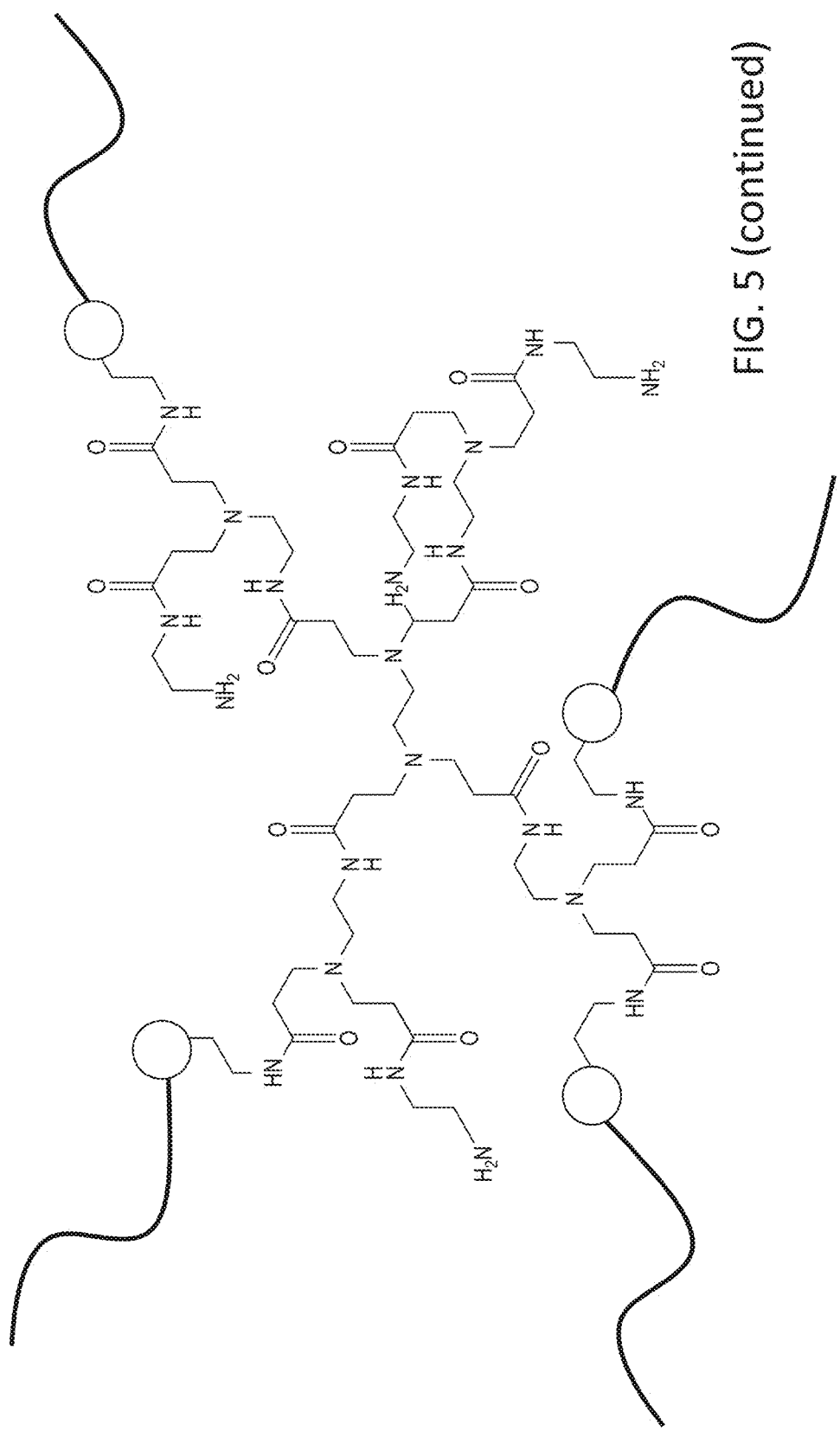
Figure 9:
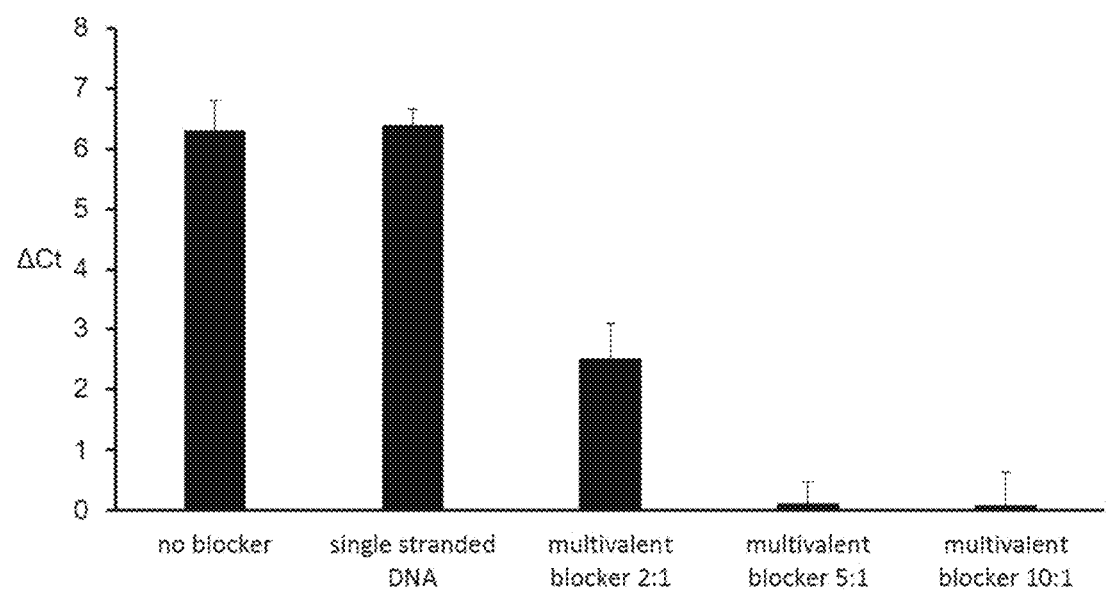
FIG. 9 shows tests of the dependence of blocking efficiency on valency. The data demonstrated bivalency alone could boost blocking efficiency significantly, and the effect plateaus at 5 DNA per blocker.

To further investigate whether this effect is indeed a result of multi-valency, we performed series of experiments. First, we synthesized three different conjugates with different valencies: 2, 5 or 10 DNA strands per dendrimer molecule (FIG. 5). In each experiment, we loaded the multi-valent blocker at the same DNA concentration into the system, so that differences in blocking efficiency could not trivially be ascribed to increased DNA content (FIG. 9). Conjugates with DNA ratios of 5:1 and 10:1 showed improved blocking activity compared to the 2:1 DNA ratio conjugate. The similar blocking efficiency of 5:1 and 10:1 DNA ratio conjugates implies that further increasing of multi-valency might not have measurable outcomes. Notably, 2:1 DNA ratio conjugates exhibit substantially higher blocking activity than normal ssDNA alone. These observations suggest that multi-valency is driving the blocking efficacy.

Figure 8:
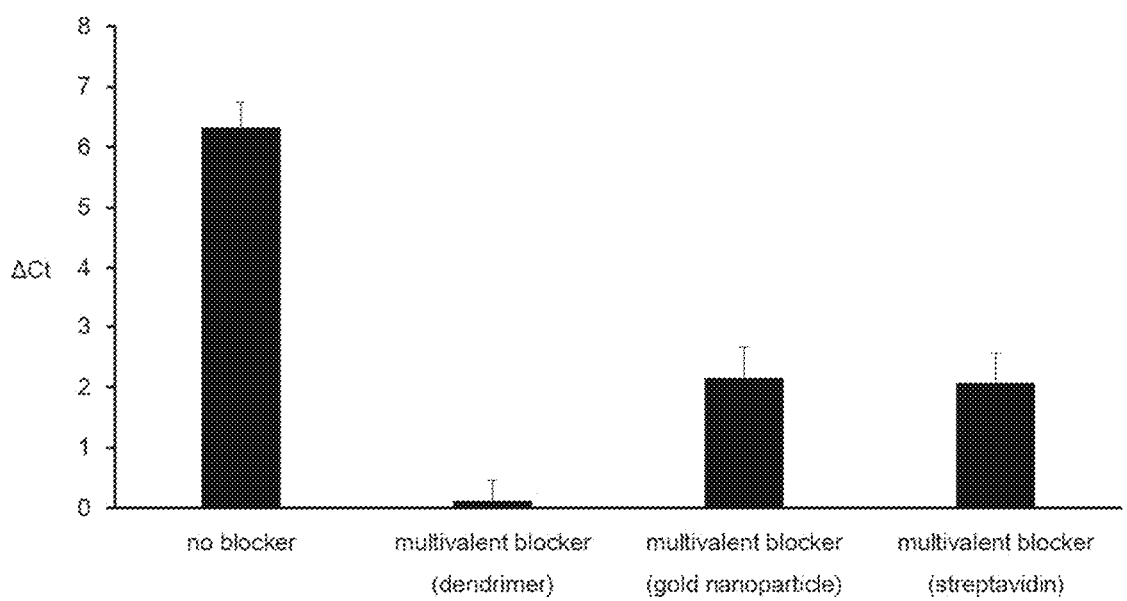
FIG. 8 shows tests of the conjugation strategy on blocking efficiency. The data demonstrated various core materials could be used for the multivalent blocker. The results unambiguously showed blocking efficiency depended on multivalence.

However, one might argue that this phenomenon is unique to dendrimer-based nucleic acid conjugates and not a result of multi-valency. For instance, one could argue that the unique linkage in the conjugation of nucleic acid and dendrimer is contributing to the blocking effect. Or one could argue the presence of a dendrimer renders the nucleic acid into a unique conformation, thereby enhancing the blocking efficacy. To preclude these possibilities, we synthesized a series of different multi-valent nucleic acids materials (FIG. 8). These included nucleic acids conjugated to a small dendrimer core (G.3, 7 kD, 2 nm size), a large dendrimer core (G6, 58 kD, 5 nm size), gold nanoparticles and streptavidin. Satisfyingly, all these different multi-valent blocking agents showed substantial improved blocking effects compared to state of the art methods (e.g. free single-stranded DNA, salmon sperm DNA and detergents). We used core scaffold materials with different sizes, different properties (organic molecules, inorganic molecules, proteins) and different linkages (co-valent or non-covalent) to unambiguously demonstrate that the only common feature among these blockers is the multi-valency of the nucleic acids. Therefore, strong evidence is provided that the multi-valency of the nucleic acid-based blocking agents is the major driver of the blocking effect.

Interestingly, among these four types of blocking materials, we observed that the G3 and G6 dendrimers share similar blocking effects (99%), gold nanoparticles (57%) and streptavidin (58%). Although we cannot explicitly confirm why dendrimer-based conjugates had superior blocking effects, we hypothesize that the weaker effects of streptavidin-based materials are because they are limited to tetrameric multi-valency at most, as streptavidin only has 4 biotin-binding pockets. The gold nanoparticles may also suffer as gold nanoparticles aggregated together during the testing process, a common behavior of these nanoparticles.

In summary, a general strategy is described to prevent non-specific binding with nucleic acid materials (FIGS. 1-4). Blocking efficiency can be markedly increased by linking multiple (2 or more) nucleic acids together to form multi-valent nucleic acid blockers. The nucleic acid portion in the nucleic blocker should carry sequences that do not interfere with the intend use. Alternatively, the nucleic acid portion of the multivalent blocker can be substituted by materials that carry negative charges such as an acrylic acid polymer. The core concept is to link multiple negatively charged materials onto a common scaffold to form a multi-valent blocker capable of blocking non-specific charge interactions with nucleic acid materials.

Figure 3:
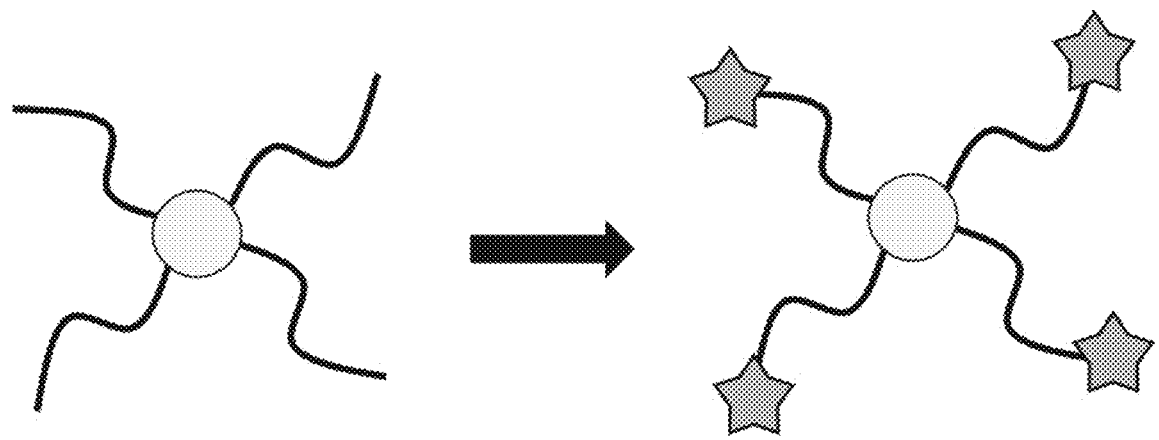
FIG. 3 shows that the multivalent negative charge blocker can be further decorated with desired modification to better mimic the actual nucleic acid reagent in the biological system. For instance, one can decorate the multivalent nucleic acid with biotin label, digoxigenin label, fluorophore label. In this way, the multi-valent blocker could also prevent non-specific binding onto the label.
Figure 4:
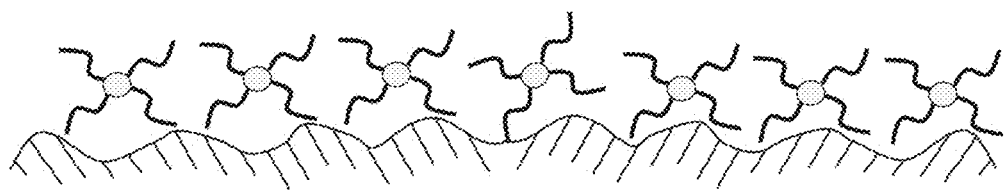
FIG. 4 shows that the multivalent nucleic acid blocker can be incubated with nucleic acids in advance to pre-occupy non-specific binding sites. Alternatively, one can introduce the target nucleic acid (e.g. aptamer, reporter labelled nucleic acid, nucleic acid conjugates, etc.) alongside the multivalent nucleic acid blocker to prevent non-specific binding from happening.
Figure 4:
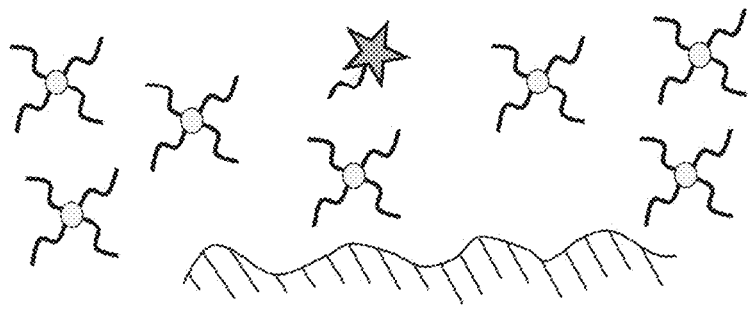

Furthermore, to further enhance the blocking performance, further modifications may be made to the multivalent blocker to make the blocker more similar to the actual nucleic acid probe (FIG. 3). For instance, if the actual nucleic acid probe carries a fluorescent tag, we can synthesize a multi-valent blocker that has the fluorescent tags attached so that the multivalent blocker also prevents non-specific binding to the fluorescent probe portion.

The multivalent blockers described in this invention can be used for essentially any biological system that uses nucleic acid materials. For instance, multivalent blockers can be used to block nonspecific interactions in assays that require nucleic acid binding to a target such as assays using aptamers (e.g. Somalogic assays) [2, 4], or any assay requiring nucleic acid hybridization such as assays using DNA/RNA microarrays, fluorescent in situ hybridization (FISH), NanoString assays [3], or next generation sequencing [9]. Multivalent blockers can also be used in any assays that require proximity of two nucleic acid probes, such as FRET, T2MR [6], and antibody-detection by agglutination PCR assays [6]. In addition, multivalent blockers can be used in any assay that uses nucleic acid labeled agents such as nucleic acid-antibody conjugates [9], nucleic acid-antigen conjugates or any other nucleic acid labeled cargos. These reagents are commonly used in immune-PCR and single-cell studies. Moreover, multivalent blockers can be used in any assays requiring the introduction of nucleic acid reagents to a specific site such as transfection, siRNA, microRNA [1], CRISPR-CAS9 assays and aptamer blocking.

The following examples and experimental methods are offered for illustrative purposes only, and are not intended to limit the scope of the present invention in any way.

EXAMPLES

Experimental Methods.

(1) Preparation of multi-valent nucleic acid blocking agent. To test the feasibility of using multi-valent nucleic acid to block non-specific interactions, we synthesized multi-valent nucleic acid reagents. Briefly, we used single-stranded DNA oligonucleotides with the following sequences as the blocking nucleic acids (Block seq: 5'-TCGTGGAACTATCTAGCGGTGTACGTGAGTGGG-CATGTAGCAAGAGGGTC-3' (SEQ ID NO: 1)). We synthesized multi-valent blocking agents using a dendrimer scaffold (FIG. 5). Dendrimers are organic molecules with repeated branches. Here we used a dendrimer based on polyamidoamine (PAMAM). PAMAM dendrimers have multiple primary amine terminal groups (amino-functional group (NH2–)), which can serve as linkage points with nucleic acids. Here, we used generation 3 PAMAM as the dendrimer core. The generation 3 dendrimer core is a relatively small molecule with a molecular weight of 6909, size of 3.6 nm and has 32 terminal amine groups on its surface. We used sulfo-SMCC (Sulfo-SMCC (sulfosuccinimidyl 4-(N15 maleimidomethyl)cyclohexane-1-carboxylate)) as a crosslinker. We incubated the PAMAM dendrimer with excess sulfo-SMCC for 2 hours at room temperature (RT). The succinimidyl-part of sulfo-SMCC reacted with the terminal amine functional groups on the dendrimer. Then, we used a size exclusion column to remove unreacted sulfo-SMCC from the sulfo-SMCC activated dendrimer. Then, we incubated the activated dendrimer with the thiolated nucleic acids (e.g., 5' thiol-TCGTGGAAC-TATCTAGCGGTGTACGTGAGTGGG-CATGTAGCAAGAGGGTC-3' (SEQ ID NO: 1)) overnight at 4° C. Importantly, the thiolated nucleic acids needed to be pre-reduced with dithiothreitol (DTT) to reduce the oxidized thiolated nucleic acids. The reduced thiol functional group of the nucleic acid reacted with the maleimide functional group on the activated SMCC-dendrimer. We could modify the incubation ratio between nucleic acids and activated dendrimer to fine tune the final DNA multi-valency. For instance, we could incubate the nucleic acid and dendrimer at 2:1, 5:1, and 10:1 ratios to make corresponding multi-valent nucleic acid blockers. The final DNA ratios were validated by gel analysis. Typically, in this reaction, one would see a distribution of DNA ratios. For instance, if DNA is incubated with a dendrimer at a 5:1 ratio, the major product produced has 5 DNA per dendrimer, but we also observed some minor bands on the gels for side products having 3:1, 4:1, 6:1, and 7:1 DNA:dendrimer ratios. Generally, the final DNA ratio on average was close to the incubated DNA to dendrimer ratio.

(2) Validate blocking efficiency of multi-valent nucleic acids. To test the blocking efficiency, we used a published antibody-detection by agglutination-PCR (ADAP) assay as a proof of principle assay (ACS Cent. Sci., 2016, 2 (3), pp 139-147). Briefly, this assay used antigen-DNA conjugates to detect presence of antibodies in a test sample. We used GFP (green fluorescent protein)-DNA conjugates in an ADAP assay to screen 50 patient sera. Theoretically, human patients should not have antibodies against GFP antigens. Therefore, one would expect no signals should be observed for these 50 patient sera. However, we identified 5 patient sera that generated very strong ADAP signals. We attributed these strong signals to non-specific interactions between substances in patient sera and the GFP-DNA conjugate probes. Then, we compared three different common blocking agents and the multi-valent nucleic acid blocking agent for their capabilities to reduce the non-specific interactions. Briefly, we used single-stranded DNA that contained the same block seq (5'-TCGTGGAAC-TATCTAGCGGTGTACGTGAGTGGG-CATGTAGCAAGAGGGTC-3'(SEQ ID NO:1)) at final concentration of 100 μM as the blocking agent. Or we used double-stranded DNA of the same sequences at final concentration of 100 μM as blocking agent. In addition, we used salmon-sperm DNA at final concentration of 1 mg/mL or dextran sulfate at a final concentration of 0.25 mg/mL as blocking agents. The concentrations we used were either on the same or slightly higher than common literature values. Thus, if these substances were effective, we should have seen the effects very evidently. Finally, we also used a multi-valent nucleic acid blocker made from a generation 3 dendrimer at a final concentration of 16 μM (the concentration is referring to the total concentration of single-stranded DNA). In other words, we incubated 1 μL of patient serum and 2 μL of probe mix (contains either none or one of the above blocking agents, 400 pM GFP-DNA conjugates, 4% BSA, 100 mM NaCl, 1×PBS pH=7.4) for 30 minutes at 37° C. Then, we performed the ligation step, pre-amplification step and final real-time quantitative PCR (qPCR) step following published ADAP protocols. The tests results are shown in FIG. 6. We observed that single-stranded DNA, double-stranded DNA and salmon-sperm DNA provided no improvement in reducing non-specific signals. Dextran sulfate reduced non-specific signals by 50%, whereas the multi-valent nucleic acid blockers reduced non-specific signals completely. Therefore, this data demonstrates that multi-valent blocking agents are superior in blocking non-specific interactions with DNA-based probes.

Figure 7:
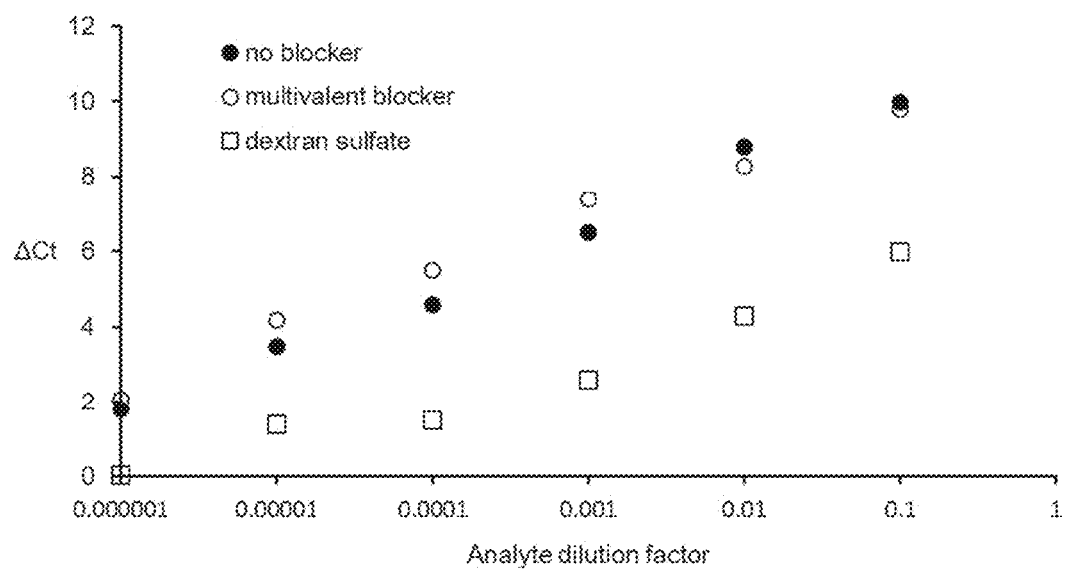
FIG. 7 shows tests of the impact of different blockers on test performance. A target analyte was serially diluted and assayed by ADAP. The data showed that the multivalent blocker did not affect assay performance, whereas dextran sulfate reduced signal intensities and assay sensitivities.

Critically, it is important to ensure blocking agents did not interfere with the assay performance. Therefore, we performed a separate ADAP experiment using p24-DNA conjugates and tested a dilution series of strongly positive HIV patient serum (which contains anti-p24 antibodies). We compared the signal intensities across dilution series between assays performed with the dextran sulfate and the multi-valent nucleic acid blocker (FIG. 7). We observed that the dextran sulfate yielded significantly reduced signals (thus lower assay sensitivity) compared to the multi-valent nucleic acid blocker. The reduced signals with dextran sulfate could be attributed to its inhibitory effect on PCR reactions, which has been widely reported in the literature. In summary, we used these experiments to demonstrate that multi-valent blockers are superior than current blocking agents in blocking non-specific interactions in nucleic acid-based assays without interfering with assay performance.

(3) Synthesizing alternative multi-valent blocking agents. In order to validate that the observed superior blocking capabilities are not unique to dendrimer-based nucleic acid conjugates, we prepared several different multi-valent blocking agent constructs. We investigated different core materials to see if we could still see similar efficient blocking behavior. We sought to confirm that the observed blocking capability is a result of multi-valency. All the single-stranded DNA we used in this experiment shared the same blocking sequences as in experiment 1. (5'-TCGTGGAAC-TATCTAGCGGTGTACGTGAGTGGG-CATGTAGCAAGAGGGTC-3' (SEQ ID NO: 1))

First, we purchased another dendrimer of larger size. We obtained generation 6 PAMAM dendrimer. This dendrimer has a molecular weight of 58 kD, size of 6.7 nm and 256 amino terminal groups. We then synthesized single-stranded DNA dendrimers following protocols outlined in experiment 1.

Secondly, we synthesized gold nanoparticles DNA conjugates. It is widely reported in the literature that thiolated DNA can be readily conjugated to gold nanoparticles. Therefore, we purchased gold nanoparticles of 2 nm and 20 nm in size. Then, we incubated these nanoparticles with thiolated single-stranded DNA. Again, the thiolated DNA had been reduced by DTT, and excess DTT was removed using a spin column (Thermo Fischer, Zeba spin desalting column, 7 kD cutoff). We incubated the DNA and nanoparticles at a 200:1 ratio with constant rotating at room temperature overnight. Then, we used centrifugation to pellet the gold nanoparticles and removed excess DNA to obtain pure DNA-nanoparticle conjugates. The successful conjugation was validated by UV-VIS spectroscopy and gel analysis. Then, we concentrated the DNA-gold nanoparticle solution to a final DNA concentration of 50 μM.

Thirdly, we synthesized streptavidin nucleic acid conjugates by incubating streptavidin with biotin-labeled single-stranded DNA. The streptavidin binds biotin-label substances with strong affinity (Kd <1 nM). Therefore, the streptavidin DNA conjugates could be synthesized readily by incubation with the biotin-labeled single-stranded DNA.

(4) Comparing performance of different multi-valent nucleic acid blockers. Then, we tested the blocking capacity of these different multi-valent nucleic acid blockers following protocols outlined in experiment 2. Briefly, we incubated 1 μL patient serum (that showed strong signals using negative control GFP-DNA conjugates) with 2 μL probe mix (that contain 400 pM GFP-DNA conjugates, one of the above multi-valent blocker at 16 μM, 100 mM NaCl, 1×PBS, pH=7.4). To fairly compare performance of different blockers, the blocker concentration is referring to the single-stranded DNA concentration. Thus, all blocking agents were loaded at concentrations so as to contain the same amount of single-stranded DNA. Then, we processed the samples by performing subsequent ligation, pre-amplification, and qPCR quantification steps. The results are shown in FIG. 8. It is evident that all multi-valent blocking agents were more efficient than single-stranded DNA alone and could reduce non-specific signals by more than 50%. This result demonstrates that various different multi-valent blocker constructs could be used to reduce non-specific binding, and strongly supports the notion that multivalency of nucleic acid is the major driver for improved blocking ability.

Furthermore, we also compared the performance of multivalent blockers with different valencies (FIG. 9). We observed that bivalency (2 DNA per blocker) alone had markedly enhanced blocking capabilities than single-stranded DNA alone. The increase in blocking efficiency seemed to plateau at pentavalency (5 DNA per blocker). This result further supports the notion that multivalency is indeed driving blocking efficiency.

REFERENCES

[1] Lu T, Lin Z, Ren J, Yao P, Wang X, Wang Z, Zhang Q. The Non-Specific Binding of Fluorescent-Labeled MiR-NAs on Cell Surface by Hydrophobic Interaction. PLOS One 2016 11(3):e0149751.

[2] Hirota M, et. al. Chemically Modified Interleukin-6 Aptamer Inhibits Development of Collagen-Induced Arthritis in Cynomolgus Monkeys. Nucleic Acid Ther. 2016 26(1):10-9.

[3] Malkov V A, Serikawa K A, Balantac N, Watters J, Geiss G, Mashadi-Hossein A, Fare T. Multiplexed measurements of gene signatures in different analytes using the Nanostring nCounter Assay System. BMC Res Notes. 2009 2:80.

[4] Gold L, et. al. Aptamer-Based Multiplexed Proteomic Technology for Biomarker Discovery. PLOS One. 2010 Dec. 7; 5(12):e15004.

[5] Tsai C T, Robinson P V, Spencer C A, Bertozzi C R. Ultrasensitive Antibody Detection by Agglutination-PCR (ADAP). ACS Cent Sci. 2016 2(3):139-147.

[6] Neely L A., et. al. T2 magnetic resonance enables nanoparticle-mediated rapid detection of candidemia in whole blood. Sci Transl Med. 2013 5(182):182ra54.

[7] Parker J, Fowler N, WalmsleyML, Schmidt T, Scharrer J, Kowaleski J, Grimes T, Hoyos S, Chen J. Analytical Sensitivity Comparison between Singleplex Real-Time PCR and a Multiplex PCR Platform for Detecting Respiratory Viruses. PLOS One. 2015 10(11):e0143164.

[8] Sanyal A, et. al. Novel assay reveals a large, inducible, replication-competent HIV-1 reservoir in resting CD4+ T cells. Nat Med. 2017 July; 23(7):885-889.

[9] Peterson V M, Zhang K X, Kumar N, Wong J, Li L, Wilson D C, Moore R, McClanahan T K, Sadekova S, Klappenbach J A. Multiplexed quantification of proteins and transcripts in single cells. Nat Biotechnol. 2017 35(10):936-939.

[10] Altman J D, Moss P A, Goulder P J, Barouch D H, McHeyzer-Williams M G, Bell J I, McMichael A J, Davis M M. Phenotypic analysis of antigen-specific T lymphocytes. Science. 1996 274(5284):94-6.

[11] Deng Z J, Liang M, Monteiro M, Toth I, Minchin R F. Nanoparticle-induced unfolding of fibrinogen promotes Mac-1 receptor activation and inflammation. Nat Nanotechnol. 2011 6(1):39-44.

Although preferred embodiments of the subject invention have been described in some detail, it is understood that obvious variations can be made without departing from the spirit and the scope of the invention as defined herein.

What is claimed is:

1. A method of blocking non-specific interactions with a nucleic acid of interest in a sample, the method comprising contacting the sample with a multivalent blocker, said multivalent blocker comprising at least three negatively charged polymers linked to a non-protein scaffold, wherein the non-protein scaffold is a positively charged dendrimer, wherein the multivalent blocker binds to positively charged compounds or materials in the sample, thereby blocking non-specific interactions with the nucleic acid of interest, wherein the negatively charged polymers are linked to the non-protein scaffold covalently or noncovalently and, wherein the nucleic acid of interest is DNA or RNA.

2. The method of claim 1, wherein the negatively charged polymers linked to the non-protein scaffold are nucleic acids, poly(acrylic acid) polymers, polysaccharides, or peptides.

3. The method of claim 1, wherein the negatively charged polymers linked to the non-protein scaffold comprise negatively charged functional groups selected from the group consisting of carboxylate, sulfate, and phosphate.

4. The method of claim 1, wherein the positively charged dendrimer is a polyamidoamine (PAMAM) dendrimer.

5. The method of claim 1, wherein the non-protein scaffold is spherical, nonspherical, linear, branched, or planar.

6. The method of claim 1, wherein the non-protein scaffold has a size ranging from about 0.3 nm to about 5 nm in length.

7. The method of claim 1, wherein the nucleic acid of interest comprises a fluorescent, bioluminescent, or chemiluminescent label.

8. The method of claim 7, wherein the multivalent blocker further comprises the same detectable label as the nucleic acid of interest.

9. The method of claim 1, further comprising performing real time quantitative polymerase chain reaction (RT-PCR), microarray analysis, fluorescent in situ hybridization (FISH), multiplex analysis, next generation sequencing, fluorescence resonance energy transfer (FRET), magnetic resonance, antibody-detection by agglutination PCR (ADAP), CRISPR-CAS9 genome editing, or transfection while blocking the non-specific interactions with the nucleic acid of interest with the multivalent blocker.

10. The method of claim 1, wherein the nucleic acid of interest is conjugated to an antibody, an antigen, a peptide, a protein, a lipid, a carbohydrate, a small molecule, a nanoparticle, or a cationic molecule.

11. The method of claim 1, wherein the nucleic acid of interest is selected from the group consisting of messenger RNA (mRNA), transfer RNA (tRNA), ribosomal RNA (rRNA), small interfering RNA (siRNA), microRNA

---

SEQUENCE LISTING

<160> NUMBER OF SEQ ID NOS: 1

<210> SEQ ID NO 1
<211> LENGTH: 50
<212> TYPE: DNA
<213> ORGANISM: Artificial Sequence
<220> FEATURE:
<223> OTHER INFORMATION: nucleic acid blocker

<400> SEQUENCE: 1
tcgtggaact atctagcggt gtacgtgagt gggcatgtag caagagggtc            50

(miRNA), short hairpin RNA (shRNA), small nuclear RNA (snRNA), long noncoding RNA (lncRNA), an RNA aptamer, and a DNA aptamer.

* * * * *